US012788544B2

(12) United States Patent
Nakano et al.

(10) Patent No.: US 12,788,544 B2
(45) Date of Patent: Nov. 10, 2026

(54) DENTAL CERAMIC OXIDE PRE-SINTERED BODY HAVING EXCELLENT MACHINABILITY AND PRODUCTION METHOD FOR SAME

(71) Applicant: KURARAY NORITAKE DENTAL INC., Kurashiki (JP)

(72) Inventors: Kirihiro Nakano, Aichi (JP); Hiroyuki Sakamoto, Aichi (JP); Nobusuke Kashiki, Aichi (JP); Shinichiro Kato, Aichi (JP); Hiroshige Ishino, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 0 days.

(21) Appl. No.: 18/722,858

(22) PCT Filed: Dec. 16, 2022

(86) PCT No.: PCT/JP2022/046470
§ 371 (c)(1),
(2) Date: Jun. 21, 2024

(87) PCT Pub. No.: WO2023/127559
PCT Pub. Date: Jul. 6, 2023

(65) Prior Publication Data

US 2025/0049547 A1 Feb. 13, 2025

(30) Foreign Application Priority Data

Dec. 27, 2021 (JP) ................................ 2021-213564

(51) Int. Cl.
*A61C 13/00* (2006.01)
*A61K 6/17* (2020.01)
(Continued)

(52) U.S. Cl.
CPC ............ *A61C 13/0022* (2013.01); *A61K 6/17* (2020.01); *A61K 6/802* (2020.01); *A61K 6/818* (2020.01); *A61C 2201/002* (2013.01)

(58) Field of Classification Search
None
See application file for complete search history.

(56) References Cited

U.S. PATENT DOCUMENTS

2011/0027742 A1 2/2011 Fujisaki et al.
2013/0065067 A1 3/2013 Nishimura et al.
(Continued)

FOREIGN PATENT DOCUMENTS

JP S62260766 A 11/1987
JP 2001213664 A 8/2001
(Continued)

OTHER PUBLICATIONS

Machine translation of WO2021100876A1 via EPO, translated Aug. 21, 2025. (Year: 2021).*
(Continued)

*Primary Examiner* — Elizabeth Collister
(74) *Attorney, Agent, or Firm* — Element IP, PLC

(57) ABSTRACT

The present invention provides an oxide ceramic pre-sintered body for dental use and a method of production thereof having excellent machinability with a low probability of chipping while exhibiting high translucency after sintering. The present invention relates to an oxide ceramic pre-sintered body for dental use comprising oxide ceramic particles with an average primary particle diameter of 50 to 300 nm, and pores, and having a D10 of 20 nm or more and a D90 of 90 nm or less in a cumulative distribution of pores within the pre-sintered body. The oxide ceramic pre-sintered body for dental use has a relative density of preferably 43 to 63%. The oxide ceramic pre-sintered body for dental use has
(Continued)

a BET specific surface area of preferably 5 to 25 $m^2/g$ as measured in compliance with JIS Z 8830:2013.

15 Claims, 2 Drawing Sheets

(51) Int. Cl.
*A61K 6/802* (2020.01)
*A61K 6/818* (2020.01)

(56) References Cited

U.S. PATENT DOCUMENTS

| | | | |
|---|---|---|---|
| 2016/0074142 | A1 | 3/2016 | Yamada et al. |
| 2020/0055779 | A1 | 2/2020 | Theelke et al. |
| 2020/0170753 | A1* | 6/2020 | Nonaka ................. C04B 35/622 |
| 2022/0098115 | A1* | 3/2022 | Yang .................. A61C 13/0022 |
| 2022/0226084 | A1 | 7/2022 | Jahns et al. |
| 2023/0295048 | A1* | 9/2023 | Camposilvan .... C04B 35/63416 501/134 |
| 2024/0010568 | A1 | 1/2024 | Nakano et al. |

FOREIGN PATENT DOCUMENTS

| | | | |
|---|---|---|---|
| JP | 2010120796 | A | 6/2010 |
| JP | 2012180275 | A | 9/2012 |
| JP | 2018030775 | A | 3/2018 |
| WO | WO-2014181828 | A1 | 11/2014 |
| WO | WO-2021100876 | A1 | 5/2021 |
| WO | WO-2022071348 | A1 | 4/2022 |

OTHER PUBLICATIONS

Amat Noor Faeizah et al., "Preparation of presintered zirconia blocks for dental restorations through colloidal dispersion and cold isostatic pressing", Ceramics International, 44, Apr. 2018, XP055783523, pp. 6409-6416.

Extended European Search Report issued Oct. 31, 2025, in corresponding European Patent Application No. 22967446.0. 9 pages.

International Search Report issued Mar. 20, 2023 in PCT/JP2022/046470 (with English translation), 5 pages.

Written Opinion of the International Searching Authority issued Mar. 20, 2023 in PCT/JP2022/046470 (with English translation), 10 pages.

High Purity Alumina HPA, Product Databook (Excerpt), Sumitomo Chemical, 2020 edition, pp. 1-17, (with English translation).

* cited by examiner

DENTAL CERAMIC OXIDE PRE-SINTERED BODY HAVING EXCELLENT MACHINABILITY AND PRODUCTION METHOD FOR SAME

TECHNICAL FIELD

The present invention relates to an oxide ceramic pre-sintered body for dental use comprising oxide ceramic particles and pores and that can be desirably milled and ground by machining, and to a method for producing such oxide ceramic pre-sintered bodies.

BACKGROUND ART

Over the last years, sintered bodies of oxide ceramics have become prevalent as dental materials. Such dental materials are used as sintered bodies that have been shaped with accurately processed dimensions and surfaces tailored to the patient and clinically affected area. Processing to the desired shape is achieved by machining such as CAD/CAM.

Aluminum oxide (alumina) and zirconium oxide (zirconia) represent examples of oxide ceramics used as dental materials. Zirconia, in particular, has seen a rising demand due to its outstanding strength and relatively superior aesthetics, propelled by the decreasing price of this material in recent years.

However, zirconia sintered bodies involve productivity and cost-related issues, such as being too hard to machine, prone to cracking during machining, prolonged machining times, and a high frequency of processing tool replacements.

Because of these issues, production of zirconia sintered bodies generally involves machining a zirconia pre-sintered body in a semi-sintered state to prepare a cut workpiece in a shape close to the desired shape resembling, for example, a tooth or a part of a tooth, instead of machining a zirconia sintered body. The cut workpiece can then be fired at or above the sintering temperature to obtain a zirconia sintered body with the desired shape. The zirconia pre-sintered body is obtained by molding a raw material powder into a disc, cuboidal, or other such shapes, and firing (or "pre-sintering" as it is also referred to hereinbelow) the resultant molded body in a temperature range that does not cause sintering.

Concerning oxide ceramics other than zirconia, examples using alumina are proposed in, for example, Patent Literatures 1 to 3. Differing in refractive index from zirconia, alumina is more advantageous in terms of translucency after sintering.

Additionally, because alumina has wide applications as sintered bodies except for porous bodies such as heat insulating materials, it is commonly practiced to obtain sintered bodies through sintering of molded bodies.

In view of dental aesthetics, the sintered bodies of oxide ceramics produced are typically polished to provide surface smoothness.

However, due to the high hardness of sintered bodies, polishing requires a significant amount of time. Moreover, remanufacturing is necessary when the surface of sintered bodies breaks (chips) during polishing. Chipping occurs in common dental oxide ceramic materials, and there exist opportunities for further improvement in these materials. Additionally, the prolonged polishing time required for sintered bodies leads to tool wear in the blade when using cutting tools. Frequent drill replacements are not economical in terms of replacement costs and continuous processing.

There accordingly is room for improvement from the perspective of productivity and economy.

CITATION LIST

Patent Literature

Patent Literature 1: JP 2001-213664 A
Patent Literature 2: JP 2012-180275 A
Patent Literature 3: JP 2010-120796 A

SUMMARY OF INVENTION

Technical Problem

The pre-sintered body is a workpiece to be cut into a cut workpiece in a shape close to the desired shape, taking into consideration the shrinkage due to sintering.

Accordingly, the surface smoothness of the pre-sintered body was not considered important.

The present inventors found that if chipping occurred during the milling process of the pre-sintered body and the surface smoothness is low before sintering, it would require a significant amount of time for polishing the sintered body after sintering, or result in an increase in the frequency or magnitude of chipping in the sintered body.

Patent Literature 1 describes a high-translucency alumina sintered body suited for dental use. However, because alumina is extensively used as sintered bodies except for porous bodies such as heat insulating materials, providing alumina as pre-sintered bodies is not essential, and no consideration is given regarding pre-sintered bodies.

In Patent Literature 1, the powder has a large median diameter D50 of 0.45 μm or greater. Consequently, there is a high probability of chipping when it is used as pre-sintered bodies for dental applications, even when adjusting the pre-sintering temperature.

Patent Literature 2 describes a method for producing an alumina sintered body, whereby a molded body obtained by using an alumina powder with an average particle diameter of 0.2 to 1.0 μm is fired at 1,480 to 1,600° C.

However, in Patent Literature 2, there is no indication of dental applications, and no consideration is given to pre-sintered bodies with high cutting properties in CAD/CAM processing.

Patent Literature 2 also involves a high probability of chipping, even when the alumina powder with an average particle diameter of 0.7 μm mentioned in Examples is used as a pre-sintered body.

Patent Literature 3 describes an alumina sintered body comprising components such as transition metal oxides, and having a fracture toughness of 4.5 $MPa \cdot m^{0.5}$ or more, and a maximum total transmittance (at a thickness of 1 mm) of 60% or more for light of 300 to 800 nm wavelength.

However, Patent Literature 3 gives no consideration to pre-sintered bodies with high cutting properties in CAD/CAM processing.

Additionally, Patent Literature 3 requires sintering under applied pressure through hot isostatic pressing (hereinafter, also referred to as "HIP") after firing, presenting a challenge in terms of achieving high cutting properties and easy manufacturing for high translucency.

In Patent Literatures 1 to 3, no consideration is given to pre-sintered bodies with excellent machinability (cutting and grinding properties) in CAD/CAM processing.

Another issue that came to be identified when machining pre-sintered bodies is the reduced tool life for cutting and grinding tools in continuous processing due to the low cutting and grinding properties of the pre-sintered bodies, leading to decreased productivity.

Conceivably, a method that employs small particles (for example, 110 nm or less) under firing conditions without HIP may produce high translucency in sintered bodies in dental applications.

However, when using small particles, the pre-sintered body becomes excessively hard, resulting in decreased workability. Indeed, it has been difficult to achieve desirable machinability in pre-sintered bodies while achieving high translucency in sintered bodies through an easy manufacturing process.

It is accordingly an object of the present invention to provide an oxide ceramic pre-sintered body for dental use having excellent machinability with a low probability of chipping while exhibiting superior translucency after sintering. Another object of the present invention is to provide a method for producing such oxide ceramic pre-sintered bodies.

Solution to Problem

The present inventors conducted intensive studies to find a solution to the foregoing issues, and found that an oxide ceramic pre-sintered body for dental use having an average primary particle diameter of 50 to 300 nm, and a specific range of pore fractions possesses excellent machinability with a low probability of chipping while exhibiting high aesthetic qualities after sintering through an easy manufacturing process.

This led to the completion of the present invention after further examinations.

Specifically, the present invention includes the following.

[1] An oxide ceramic pre-sintered body for dental use comprising oxide ceramic particles with an average primary particle diameter of 50 to 300 nm, and pores, and having a D10 of 20 nm or more and a D90 of 90 nm or less in a cumulative distribution of pores.

[2] The oxide ceramic pre-sintered body for dental use according to [1], which has a relative density of 43 to 63%.

[3] The oxide ceramic pre-sintered body for dental use according to [1] or [2], which has a BET specific surface area of 5 to 25 $m^2/g$ as measured in compliance with JIS Z 8830:2013.

[4] The oxide ceramic pre-sintered body for dental use according to any one of [1] to [3], which has a three-point flexural strength of 10 to 50 MPa as measured in compliance with JIS R 1601:2008.

[5] The oxide ceramic pre-sintered body for dental use according to any one of [1] to [4], which has a Vickers hardness of 350 HV 5/30 or less as measured in compliance with JIS Z 2244:2020.

[6] The oxide ceramic pre-sintered body for dental use according to any one of [1] to [5], wherein the oxide ceramic particles comprise zirconia and/or alumina.

[7] The oxide ceramic pre-sintered body for dental use according to [6], wherein the alumina comprises α-alumina with a purity of 99.5% or more.

[8] The oxide ceramic pre-sintered body for dental use according to [6] or [7], which further comprises a sintering aid, and the sintering aid comprises at least one element selected from the group consisting of a Group 2 element, Ce, Zr, and Y.

[9] The oxide ceramic pre-sintered body for dental use according to any one of [1] to [8], which, after being fired into a sintered body at 1,400° C. or less without hot isostatic pressing, shows a translucency (ΔL) of 9 or more as a sintered body of 1.2 mm thickness, and a total transmittance of 27% or more and a linear light transmittance of 0.5% or more as a sintered body of 1.0 mm thickness under a D65 illuminant.

[10] The oxide ceramic pre-sintered body for dental use according to any one of [1] to [9], which shows a number-based average crystal grain size of 0.3 to 8.0 μm after being fired into a sintered body at 1,400° C. or less without hot isostatic pressing.

[11]A method for producing an oxide ceramic pre-sintered body for dental use, comprising the steps of:

- press molding an oxide ceramic composition under a surface pressure of 5 to 600 MPa; and
- firing the resultant molded body at 400 to 1,300° C. under atmospheric pressure,
- the oxide ceramic pre-sintered body for dental use comprising oxide ceramic particles with an average primary particle diameter of 50 to 300 nm, and having a D10 of 20 nm or more and a D90 of 90 nm or less in a cumulative distribution of pores.

[12] The method for producing an oxide ceramic pre-sintered body for dental use according to [11], wherein the oxide ceramic particles comprise zirconia and/or alumina.

[13] The method for producing an oxide ceramic pre-sintered body for dental use according to [11] or [12], wherein the alumina comprises α-alumina with a purity of 99.5% or more.

[14]A method for producing an oxide ceramic sintered body for dental use, comprising the step of sintering a pre-sintered body of any one of [1] to [10] under atmospheric pressure without hot isostatic pressing.

Advantageous Effects of Invention

According to the present invention, an oxide ceramic pre-sintered body for dental use can be provided that has excellent machinability with a low probability of chipping (hereinafter, also referred to as "chipping rate") while exhibiting high translucency after sintering. The invention can also provide a method for producing such oxide ceramic pre-sintered bodies.

According to the present invention, excellent machinability reduces the amount of tool wear and chipping rate, resulting in a lower replacement frequency of cutting tools (for example, milling burs), high continuous productivity, and reduced need for rework or remanufacturing in dental applications. This has led to the provision of an oxide ceramic pre-sintered body for dental use having high productivity and cost-effectiveness. Because no HIP processing is required and the shrinkage rate is uniform, an oxide ceramic sintered body for dental use can be provided that has high productivity and high translucency.

The present invention can also provide an oxide ceramic pre-sintered body for dental use that undergoes shrinkage at a uniform rate during sintering, and a method of production of such oxide ceramic pre-sintered bodies.

DESCRIPTION OF EMBODIMENTS

Figure 1:
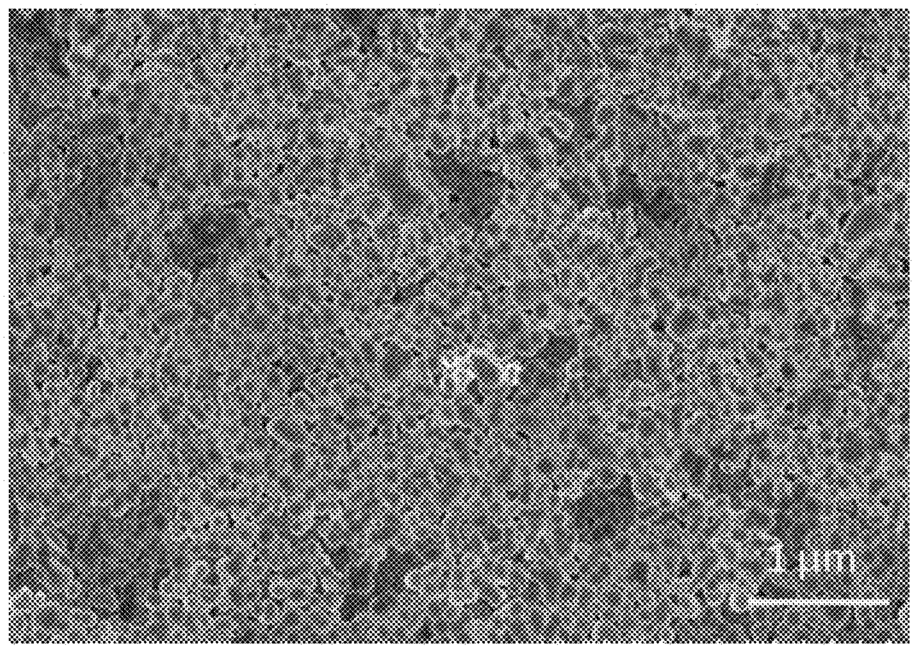
FIG. 1 An electron micrograph of a cross section of a pre-sintered body according to Example 1.

An oxide ceramic pre-sintered body for dental use of the present invention comprises oxide ceramic particles with an average primary particle diameter of 50 to 300 nm, and pores, and has a D10 of 20 nm or more and a D90 of 90 nm or less in a cumulative distribution of pores within the pre-sintered body.

A pre-sintered body of the present invention is described below.

The pre-sintered body can be a precursor (intermediate product) of a sintered body.

In this specification, "pre-sintered body" refers to a state where oxide ceramic particles have formed necks, and have solidified without being fully sintered.

The pre-sintered body may have a predetermined shape (for example, such as a disc shape or cuboidal shape).

The pre-sintered body may be a workpiece that has been processed into, for example, a crown shape. The pre-sintered body will be referred to as "workpiece" or "cut workpiece" when it has been processed.

The workpiece can be obtained by, for example, processing an oxide ceramic disc (pre-sintered body) into a dental product (for example, a crown-shaped prosthesis) with the CAD/CAM (Computer-Aided Design/Computer-Aided Manufacturing) system.

A pre-sintered body of the present invention comprises necked particles formed of oxide ceramics (hereinafter, also referred to simply as "oxide ceramic particles"), and the extent of necking varies with the average particle diameter of these particles, resulting in a change in the hardness of the pre-sintered body. The smaller the average primary particle diameter of the oxide ceramic particles, the more likely necking takes place during pre-sintering.

In view of an amount of tool wear and/or chipping related to machinability, the oxide ceramic particles contained in a pre-sintered body of the present invention have an average primary particle diameter of 50 to 300 nm. When the particles have an average primary particle diameter of more than 300 nm, the localized presence of coarse particles leads to increased chipping. An average primary particle diameter of more than 300 nm is also not preferable because it leads to an increase in crystal grain size after sintering, resulting in a decrease in translucency and strength as dental materials. An average primary particle diameter of less than 50 nm leads to an increase in the number of necks between particles, resulting in a harder pre-sintered body and larger amounts of tool wear. An average primary particle diameter of 50 nm or more is preferable because it does not lead to strong necking, making it less likely to cause an increase in hardness, enabling a reduction in the amount of tool wear. An average primary particle diameter of 300 nm or less is preferable because the incorporation of smaller particles in the particle size distribution becomes less likely, reducing the occurrence of necking due to particle size differences, reducing the amount of tool wear and chipping rate. The average primary particle diameter of the particles is preferably 60 to 250 nm, more preferably 70 to 200 nm, even more preferably 80 to 180 nm. The method of measurement of the average primary particle diameter in the pre-sintered body is as described in the EXAMPLES section below.

A pre-sintered body of the present invention internally comprises continuous holes (pores). The pores ensure space for particle movement when cutting and grinding tools come into contact with the pre-sintered body, reducing cutting and grinding resistance, enabling a reduction in the amount of tool wear.

In a pre-sintered body of the present invention, the amount of tool wear and chipping rate are reduced when D10 is 20 nm or more and D90 is 90 nm or less in the cumulated pore distribution (cumulative distribution of pores). With D10 and D90 falling in these ranges, the pre-sintered body can have an increased number of gaps, allowing it to achieve an excellent balance between machinability and properties such as translucency as a sintered body after sintering.

In this specification, D10 and D90 refer to pore diameters corresponding to the cumulative 10% and cumulative 90%, respectively, of pore diameters in a cumulative pore distribution, starting from smaller values.

The measurement of the cumulative distribution of pores, including D10 and D90, can be conducted using a method in compliance with JIS R 1655:2003.

The measurement method of cumulative pore distribution is specifically described in the EXAMPLES section below.

With a D10 of 20 nm or more in a cumulative distribution of pores, the voids are not excessively small with respect to particles with an average primary particle diameter of 50 to 300 nm. That is, it is possible to reduce excessive necking, enabling a significant decrease in the amount of tool wear.

In view of machinability and a reduction of chipping rate, D10 is preferably 25 nm or more, more preferably 30 nm or more, even more preferably 36 nm or more, most preferably 39 nm or more.

With a D90 of 90 nm or less in a cumulative distribution of pores, it is possible to prevent coarseness in density or reduce the localized presence of coarse particles within the pre-sintered body with respect to particles having an average primary particle diameter of 50 to 300 nm, enabling a significant decrease in chipping rate.

In view of a reduction of chipping rate, D90 is preferably 80 nm or less, more preferably 75 nm or less, even more preferably 70 nm or less, most preferably 66 nm or less.

In view of a reduction of chipping rate, the ratio D10/D90 is preferably 1.0 or less, more preferably 0.9 or less, even more preferably 0.8 or less, most preferably 0.6 or less in a pre-sintered body of the present invention.

In view of a reduction of chipping rate, the ratio D10/D90 is preferably 0.1 or more, more preferably 0.15 or more, even more preferably 0.2 or more, most preferably 0.3 or more in a pre-sintered body of the present invention.

A certain preferred embodiment is, for example, an oxide ceramic pre-sintered body for dental use with a ratio D10/D90 of 0.32 to 0.59.

In a pre-sintered body of the present invention, the relative density can be controlled by the method of production described later.

A relative density of less than 43% means that the proportion of pores inside the pre-sintered body is high, leading to increased chipping due to sparsity in the relative density inside the pre-sintered body. This sparsity results in uneven shrinkage rates during sintering, causing some deformation in the sintered body, increasing the need for reworking in processes such as machining.

In view of the translucency of the sintered body, it is not preferable to have sparsity in relative density. This is because, though the presence of sparsity may improve machinability (cutting and grinding properties), a high proportion of pores within the pre-sintered body means that the distance between particle is large, resulting in the inability to completely release voids out of the sintered body during the sintering process, leading to a decrease in properties such as translucency and linear light transmittance in the sintered body.

The relative density in a pre-sintered body of the present invention is preferably 43 to 63%. Within this range, there is a good overall balance between particles and pores, leading to an improved balance in performance between machinability and post-sintering translucency. This enables a reduction in the amount of tool wear and/or chipping rate, allowing for the maintenance of high levels of translucency in the sintered body. Because the overall balance between particles and pores can improve with the relative density falling in the predetermined range, it is possible to achieve a uniform shrinkage rate with no unevenness.

The relative density is more preferably 45 to 60%, even more preferably 47% to 57%.

The relative density of the pre-sintered body can be calculated from the porosity of the pre-sintered body. Specifically, a mercury porosimeter can be used for the measurement and calculation of relative density.

The mercury porosimeter is preferably one capable of applying a mercury pressure of 15 to 30,000 psia, preferably 0.5 to 60,000 psia.

In view of reducing measurement errors, the preferred pressure resolution is 0.1 psia or higher.

Examples of the mercury porosimeter include AutoPore© IV 9500, manufactured by Micromeritics (USA).

The density of the pre-sintered body is defined as the density of a pre-sintered body obtained after granules resulting from drying of raw materials are filled into a specific mold (such as a die) and molded into a specific shape under pressure, and the resulting molded body is subsequently heated to remove organic components (such as binders) at a temperature that allows for removal of organic components, and heated again at a temperature that allows for moderate formation of a solid solution with yttria, and a moderate level of necking.

The temperature for the removal of organic components is not particularly limited, as long as it allows for removal of organic components such as binders. The temperature can be selected according to the type of binder or other organic components, and may be 150 to 500° C.

The temperature at which moderate neck formation occurs is preferably 400 to 1,300° C.

Details will be described later in conjunction with the pre-sintering temperature.

A pre-sintered body of the present invention exhibits a change in BET specific surface area with the average primary particle diameter, state of necking, and density, including relative density.

The BET specific surface area can be measured in compliance with JIS Z 8830:2013. For the measurement of BET specific surface area, commercially available products can be used, such as a full automatic specific surface area analyzer (manufactured by Mountech Co., Ltd. under the trade name Macsorb© HM Model-1200, BET flow method (single point/multi point)).

In view of reducing the amount of tool wear and chipping rate, a pre-sintered body of the present invention has a BET specific surface area of preferably 5 to 25 $m^2/g$, more preferably 7.5 $m^2/g$ or more, even more preferably 8 $m^2/g$ or more.

With a BET specific surface area of 5 $m^2/g$ or more, the average primary particle diameter is not excessively large, allowing for the reduction of an increase in chipping rate, and the prevention of excessive necking, thereby reducing an increase in the amount of tool wear.

The BET specific surface area is preferably 25 $m^2/g$ or less, more preferably 22 $m^2/g$ or less, even more preferably 18 $m^2/g$ or less.

With a BET specific surface area of 25 $m^2/g$ or less, the average primary particle diameter is not excessively small, preventing the pre-sintered body from becoming overly hard. This facilitates a reduction in the amount of tool wear and/or chipping rate, or allows for a reduction of density coarseness by ensuring sufficient necking, making it easier to reduce the chipping rate.

In this specification, "BET specific surface area" refers to the specific surface area measured without distinguishing between primary particles and secondary particles.

Concerning the BET specific surface area of a pre-sintered body of the present invention and the BET specific surface area of the composition mentioned later, the extent of necking is preferably such that the numerical difference obtained by subtracting the BET specific surface area of the pre-sintered body from the BET specific surface area of the composition is within 10 $m^2/g$. This makes it possible to maintain good machinability (cutting and grinding properties).

The machinability of the pre-sintered body is also influenced by the strength of the pre-sintered body in a pre-sintered body of the present invention.

The strength of a pre-sintered body according to the present invention can be evaluated by measuring the flexural strength of the pre-sintered body, for example.

The three-point flexural strength of a pre-sintered body according to the present invention can be measured in compliance with JIS R 1601:2008.

In order to ensure strength that enables machining, the pre-sintered body has a three-point flexural strength of preferably 10 MPa or more, more preferably 15 MPa or more, even more preferably 20 MPa or more.

When the pre-sintered body has a three-point flexural strength of 10 MPa or more, the pillar (support or sprue) does not break during cutting, and can remain attached to the pre-sintered body until it becomes a cut workpiece.

For easy machining, the pre-sintered body has a three-point flexural strength of preferably 50 MPa or less, more preferably 45 MPa or less, even more preferably 40 MPa or less, particularly preferably 35 MPa or less.

In view of reducing the amount of tool wear or chipping rate, and enabling easy separation of the cut workpiece from the fixture frame for quick removal while reducing tool wear, a pre-sintered body of the present invention has a Vickers hardness of preferably 350 HV 5/30 or less, more preferably 300 HV 5/30 or less, even more preferably 100 HV 5/30 or less.

Here, "HV 5/30" means a Vickers hardness under the application of a load (test force) of 5 kgf for a duration of 30 seconds.

A pre-sintered body of the present invention can have a reduced probability of chipping with the Vickers hardness falling in the foregoing predetermined ranges, along with the predetermined ranges of cumulative distributions of pores within the pre-sintered body.

The Vickers hardness in the present invention is measured using a method in compliance with JIS Z 2244:2020, as will be described later in detail in the EXAMPLES section.

A pre-sintered body of the present invention undergoes shrinkage with the firing temperature. For example, when the orthogonal three sides of a cuboidal press-molded body are denoted as X, Y, and Z each with an initial length of 100%, the press-molded body experiences approximately 1% shrinkage on average in the X, Y, and Z directions while transforming into a pre-sintered body through a pre-sintering process, and shrinks approximately 20% on average in the X, Y, and Z directions when transformed into a sintered body.

In view of suitability as dental materials, a pre-sintered body of the present invention can be used after being cut into a workpiece by, for example, CAD/CAM, taking into account the anticipated shrinkage rate in each of the X, Y, and Z directions, so that the pre-sintered body can transform into a sintered body of the desired shape after sintering by undergoing shrinkage during the firing process.

The shrinkage rate from the molded body or pre-sintered body to the sintered body may vary independently in the X, Y, and Z directions. However, if there is localized variation in shrinkage rate within the same pre-sintered body, for example, in the X direction, it leads to localized shrinkage in the process of forming a sintered body from the workpiece obtained through a machining process, for example, such as CAD/CAM. Because this results in the inability to achieve the desired shape for the sintered body, it is preferable that the shrinkage rate be uniform in the X, Y, and Z directions.

It is important for the pre-sintered body to have a uniform shrinkage rate along a given direction, particularly because the shrinkage rate from the pre-sintered body to the sintered body exceeds the shrinkage rate from the molded body to the pre-sintered body.

The uniformity of shrinkage rate in the pre-sintered body can be assessed by, for example, cutting the pre-sintered body into a number of cubes smaller than the pre-sintered body, firing the cubes, and comparing the shrinkage rates before and after sintering in X, Y, or Z direction for each cube.

As an example, a disc-shaped pre-sintered body with a thickness of 14 mm and a diameter of 98.5 mm is cut into a set number of 5-mm square cubes, and the difference between the X, Y, or Z shrinkage rate and the average shrinkage rate is calculated as the shrinkage rate deviation.

Lower absolute values of this deviation mean more uniform shrinkage. The absolute value of shrinkage rate deviation is preferably within 0.4%. Confining the absolute value of shrinkage rate deviation within 0.4% is preferable because it can reduce the risk of localized deformations when the pre-sintered body is sintered after being cut into a desired shape as a dental material.

The absolute value of shrinkage rate deviation is more preferably within 0.35%, even more preferably within 0.3%, most preferably within 0.25%.

The oxide ceramic particles used in the present invention are not particularly limited, and include those containing, for example, zirconia, alumina, titania, silica, niobium oxide, tantalum oxide, and yttria. The oxide ceramics may be used alone, or two or more thereof may be used in combination. In view of enhancing the aesthetic qualities and strength of the sintered body as a dental material, the oxide ceramic particles are preferably those containing zirconia and/or alumina, more preferably those containing zirconia and/or alumina as main components.

The following describes embodiments where oxide ceramic particles contain alumina as a main component, while also discussing situations where the oxide ceramic is zirconia, as needed.

A composition containing alumina as a main component among the aforementioned oxide ceramics is preferable because of its ability to enhance the aesthetic qualities (primarily translucency) of the sintered body as a dental material, as well as exhibiting excellent chemical stability. Among variants of alumina, α-alumina with a purity of 99.5% or more is more preferred for its low impurity content, and the ability to reduce the impurity-related formation of a glass phase at crystal grain boundaries, prevent the coarsening of crystal grains (grains), and inhibit a decrease of aesthetic qualities in the sintered body as a dental material.

Using α-phase aluminum oxide (α-alumina) as the starting raw material is preferable because, with its high corrosiveness and stability at elevated temperatures, it enables uniform control of the pre-sintered body, and facilitates easier reduction of the amount of tool wear or chipping rate, in addition to enabling densification of grain size in the crystalline structure within the sintered body.

Considering these factors, it is particularly preferable that the alumina particles contained in a pre-sintered body of the present invention comprise α-alumina particles with a purity of 99.5% or more.

The alumina raw material can be acquired using methods, for example, such as the alkoxide method, modified Bayer method, ammonium alum pyrolysis method, and ammonium dawsonite pyrolysis method, preferably the alkoxide method. The alkoxide method allows for enhancement of purity in a powder of alumina raw material, making it easier to achieve a uniform particle size distribution. As a specific example, aluminum hydroxide obtained through hydrolysis of purified aluminum alkoxide is fired in air at 1,100° C. or higher temperatures.

Examples of the alumina raw material include α-alumina with a purity 99.99% or more manufactured as the NXA grade by Sumitomo Chemical Co., Ltd. (e.g., NXA-100, NXA-150, ultrafine α-alumina).

The following describes an alumina pre-sintered body, taking aluminum oxide as an example of the oxide ceramic. Should zirconium oxide be chosen as the oxide ceramic, it can be implemented in the same fashion as a zirconia composition, except where specified otherwise.

In view of enhancing strength after sintering, and providing high aesthetic qualities in particular, an alumina pre-sintered body of the present invention preferably comprises a sintering aid (an auxiliary agent that accelerates and stabilizes sintering of alumina).

The sintering aid contained in an alumina pre-sintered body of the present invention preferably comprises at least one element selected from the group consisting of a Group 2 element (Be, Mg, Ca, Sr, Ba, Ra), Ce, Zr, and Y, more preferably at least one element selected from the group consisting of Mg, Ca, Sr, Ba, Ce, Zr, and Y, even more preferably at least one element selected from the group consisting of Mg, Ce, Zr, and Y.

The sintering aid is most preferably a magnesium compound.

Examples of the magnesium compound include oxides, nitrates, acetates, hydroxides, and chlorides.

Examples of the sintering aid include $MgCl_2$, $Mg(OH)_2$, $CeO_2$, $ZrO_2$, and $Y_2O_3$.

The magnesium compound as a sintering aid is not limited, as long as it is a magnesium compound that turns into an oxide at 1,200° C. or less during a sintering process in the atmosphere. Most preferred examples include magnesium nitrate, magnesium chloride, magnesium hydroxide, and magnesium acetate.

The sintering aid may be used alone, or two or more thereof may be used in combination.

Generally, the content of the sintering aid in a powder of alumina raw materials according to the present invention is preferably 10 ppm to 5,000 ppm, more preferably 20 ppm to 3,000 ppm, even more preferably 50 ppm to 1,500 ppm in terms of the aforementioned elements (for example, in terms of a Mg element). In this specification, ppm means ppm by mass.

When the content of the sintering aid (preferably, a magnesium compound) is low, it may result in a sintered body with a shade whiter than natural teeth, whereas an excessive content may impart an overly strong red tint.

The mechanism by which the sintering aid enhances sintering density is believed to involve the exclusion of pores from the system by preventing the pores from being integrated into the grains, probably as a result of the sintering aid existing as a distinct phase at the grain boundaries, and inhibiting the growth and propagation of grain boundaries.

In applications requiring a sintered body with high purity, for example, 99.99 mass % or more, the content of the sintering aid in the alumina powder may be 10 to 100 ppm, or 20 to 50 ppm, in terms of the constituent element of the sintering aid (for example, in terms of a Mg element). The content of the sintering aid in an alumina pre-sintered body of the present invention and in the alumina composition mentioned later aligns with the content of the sintering aid in the alumina powder.

A certain preferred embodiment (X-1) is, for example, an oxide ceramic pre-sintered body for dental use comprising oxide ceramic particles with an average primary particle diameter of 50 to 300 nm, and pores, and having a relative density of 43 to 63%, and a D10 of 20 nm or more and a D90 of 90 nm or less in a cumulative distribution of pores within the pre-sintered body.

In the embodiment (X-1), the oxide ceramic pre-sintered body for dental use has a BET specific surface area of preferably 5 to 25 $m^2/g$.

In the embodiment (X-1), the oxide ceramic pre-sintered body for dental use has a three-point flexural strength of preferably 10 to 50 MPa.

In the embodiment (X-1), the oxide ceramic pre-sintered body for dental use has a Vickers hardness of preferably 350 HV 5/30 or less as measured in compliance with JIS Z 2244:2020.

In the embodiment (X-1), the oxide ceramic particles preferably comprise zirconia and/or alumina.

Another certain preferred embodiment (X-2) is, for example, an oxide ceramic pre-sintered body for dental use comprising oxide ceramic particles with an average primary particle diameter of 50 to 300 nm, and pores, and having a BET specific surface area of 5 to 25 $m^2/g$, and a D10 of 20 nm or more and a D90 of 90 nm or less in a cumulative distribution of pores within the pre-sintered body.

In the embodiment (X-2), the oxide ceramic pre-sintered body for dental use has a three-point flexural strength of preferably 10 to 50 MPa.

In the embodiment (X-2), the oxide ceramic pre-sintered body for dental use has a Vickers hardness of preferably 350 HV 5/30 or less as measured in compliance with JIS Z 2244:2020.

In the embodiment (X-2), the oxide ceramic particles preferably comprise zirconia and/or alumina.

Yet another certain preferred embodiment (X-3) is, for example, an oxide ceramic pre-sintered body for dental use comprising oxide ceramic particles with an average primary particle diameter of 50 to 300 nm, and pores, and having a three-point flexural strength of 10 to 50 MPa, and a D10 of 20 nm or more and a D90 of 90 nm or less in a cumulative distribution of pores within the pre-sintered body.

In the embodiment (X-3), the oxide ceramic pre-sintered body for dental use has a Vickers hardness of preferably 350 HV 5/30 or less as measured in compliance with JIS Z 2244:2020.

In the embodiment (X-3), the oxide ceramic particles preferably comprise zirconia and/or alumina.

Still another certain preferred embodiment (X-4) is, for example, an oxide ceramic pre-sintered body for dental use comprising oxide ceramic particles with an average primary particle diameter of 50 to 300 nm, and pores, and having a Vickers hardness of 350 HV 5/30 or less as measured in compliance with JIS Z 2244:2020, and a D10 of 20 nm or more and a D90 of 90 nm or less in a cumulative distribution of pores within the pre-sintered body.

In the embodiment (X-4), the oxide ceramic particles preferably comprise zirconia and/or alumina.

Yet another certain preferred embodiment (X-5) is, for example, an oxide ceramic pre-sintered body for dental use comprising oxide ceramic particles with an average primary particle diameter of 50 to 300 nm, and pores, and having a D10 of 20 nm or more and a D90 of 90 nm or less in a cumulative distribution of pores within the pre-sintered body, with the oxide ceramic particles comprising alumina.

In the embodiment (X-5), the alumina preferably comprises $\alpha$-alumina with a purity of 99.5% or more.

In the embodiment (X-5), it is preferable that the oxide ceramic pre-sintered body for dental use further comprise a sintering aid, and the sintering aid comprise at least one element selected from the group consisting of a Group 2 element, Ce, Zr, and Y.

A certain preferred embodiment (Y-1) is, for example, an oxide ceramic pre-sintered body for dental use comprising oxide ceramic particles with an average primary particle diameter of 50 to 300 nm, and pores, and having a relative density of 43 to 63%.

In the embodiment (Y-1), the oxide ceramic pre-sintered body for dental use has a BET specific surface area of preferably 5 to 25 $m^2/g$.

In the embodiment (Y-1), the oxide ceramic pre-sintered body for dental use has a three-point flexural strength of preferably 10 to 50 MPa.

In the embodiment (Y-1), the oxide ceramic pre-sintered body for dental use has a Vickers hardness of preferably 350 HV 5/30 or less as measured in compliance with JIS Z 2244:2020.

In the embodiment (Y-1), the oxide ceramic pre-sintered body for dental use has a ratio D10/D90 of preferably 1.5 or less.

In the embodiment (Y-1), it is preferable that the oxide ceramic pre-sintered body for dental use further comprise a sintering aid, and the sintering aid comprise at least one element selected from the group consisting of a Group 2 element, Ce, Zr, and Y.

In the embodiment (Y-1), the oxide ceramic particles preferably comprise zirconia and/or alumina.

A certain embodiment (Z-1) is, for example, an oxide ceramic pre-sintered body for dental use comprising oxide ceramic particles and pores, and having a D10 of 20 nm or more and a D90 of 90 nm or less in a cumulative distribution of pores within the pre-sintered body.

Another embodiment (Z-2) is, for example, an oxide ceramic pre-sintered body for dental use comprising oxide ceramic particles and pores, and having a relative density of 43 to 63%, and a D10 of 20 nm or more and a D90 of 90 nm or less in a cumulative distribution of pores within the pre-sintered body.

In any of the foregoing embodiments (X-1) to (X-5), (Y-1), and (Z-1) and (Z-2), various changes (additions, deletions, substitutions, combinations) may be appropriately applied to the types and quantities of any configurations and components among the various configurations and components, based on the descriptions of this specification.

In any of the foregoing embodiments, it is also possible to appropriately change and combine the configurations and components of each pre-sintered body and its properties (such as translucency (ΔL), and total transmittance and linear light transmittance under a D65 illuminant). For example, the pre-sintered bodies of embodiments (X-1) to (X-5), (Y-1), and (Z-1) and (Z-2) may have a linear light transmittance of 0.5% or more after being fired into a sintered body at 1,400° C. or less.

Another certain preferred embodiment is, for example, an oxide ceramic pre-sintered body for dental use comprising zirconia.

The main components of the oxide ceramics contained in a pre-sintered body of the present invention may be zirconia, and a stabilizing agent capable of preventing a phase transformation of zirconia (hereinafter, also referred to simply as "stabilizing agent"). The stabilizing agent is preferably one capable of forming partially-stabilized zirconia. Examples of the stabilizing agent include calcium oxide (CaO), magnesium oxide (MgO), yttria, cerium oxide ($CeO_2$), scandium oxide ($Sc_2O_3$), niobium oxide ($Nb_2O$), lanthanum oxide ($La_2O_3$), erbium oxide ($Er_2O_3$), praseodymium oxide ($Pr_6O_{11}$, $Pr_2O_3$), samarium oxide ($Sm_2O_3$), europium oxide ($Eu_2O_3$), and thulium oxide ($Tm_2O_3$). Preferred is yttria.

In the case of a pre-sintered body comprising zirconia as the main component of the oxide ceramic (hereinafter, also referred to simply as "zirconia pre-sintered body"), it is preferable in a zirconia pre-sintered body of the present invention and a sintered body thereof that the content of the stabilizing agent (preferably, yttria) be 3.0 to 8.0 mol %, more preferably 3.2 to 6.5 mol %, even more preferably 3.5 to 6.0 mol %, particularly preferably 3.9 to 5.4 mol % relative to the total mole of zirconia and the stabilizing agent.

When the content of stabilizing agent is less than 3.0 mol %, it leads to a zirconia sintered body with insufficient translucency. When the content of stabilizing agent is more than 8.0 mol %, it leads to an elevated presence of a phase transforming into the tetragonal and/or cubic crystal systems, resulting in an increased chipping rate and a strength reduction in the zirconia sintered body.

The content of the sintering aid or stabilizing agent in a pre-sintered body of the present invention and in a sintered body thereof can be measured by, for example, inductively coupled plasma (ICP) emission spectral analysis, X-ray fluorescence analysis (XRF), scanning or transmission electron microscopy (SEM or TEM), energy dispersive X-ray analysis or wavelength dispersive X-ray analysis (EDX or WDX), or field emission electron probe microanalysis (FE-EPMA).

In dental products, surface smoothness is important in terms of translucency, and it is preferable to have a low chipping rate in the pre-sintered body. A low chipping rate is also preferred in terms of reducing the effort needed for reworking the cut workpiece as a dental material after firing. The chipping rate is preferably 10% or less, more preferably 7% or less, even more preferably 3% or less. The method of measurement of chipping rate is as described in the EXAMPLES section below.

The following describes an oxide ceramic composition for producing an oxide ceramic pre-sintered body of the present invention, taking an alumina composition as an example where the oxide ceramic is aluminum oxide. The term "alumina composition" can be read as referring to "oxide ceramic composition", except where specified otherwise. Similarly, should zirconium oxide be chosen as the oxide ceramic, it can be implemented in the same fashion as a zirconia composition, except where specified otherwise.

The alumina composition becomes a precursor of an alumina pre-sintered body of the present invention.

In this specification, the alumina composition and molded body refer to a state before firing, and involve no necking between alumina particles.

The content of alumina and sintering aids in an alumina composition of the present invention is calculated from their content in a predetermined alumina pre-sintered body, and is the same for the alumina composition and alumina pre-sintered body.

The form of the alumina composition is not limited, and an alumina composition of the present invention may have various forms, including a powder, a fluid with a powder added to solvent, and a molded body of a powder formed into a predetermined shape. When an alumina composition of the present invention has a powder form, it may be a cluster of granules. The granules are formed by the aggregation of primary particles.

In this specification, "primary particle" refers to a bulk representing the smallest unit. For example, "primary particle" refers to particles that appear spherical under an electron microscope (for example, a scanning electron microscope). The primary particles include alumina particles. When employing particulate sintering aids, the primary particles include particles of sintering aid, as well as alumina particles.

Preferably, the particles constituting the granules formed of the alumina composition are predominantly primary particles. Aggregates of primary particles are referred to as secondary particles. Preferably, the number of primary particles is greater than the number of secondary particles in visual confirmation through, for example, an electron microscope. Secondary particles are typically irregular in shape, and an increase in their quantity leads to sparse density during the press molding process described later, resulting in increased chipping.

The particle diameter of primary particles within the particles constituting the granules formed of the alumina composition influences the extent of necking during pre-sintering, and affects the hardness of the pre-sintered body. Particles with an average primary particle diameter of less than 50 nm are not preferable because such particles cause strong necking, leading to a reduction in the surface area of primary particles within the pre-sintered body, resulting in increased hardness. An average primary particle diameter of larger than 300 nm is not preferable because it increases the likelihood of the incorporation of smaller particles in the particle size distribution, resulting in the occurrence of localized necking due to particle size differences and leading to increased coarseness in density. The preferred range is 50 to 300 nm, more preferably 60 to 250 nm, even more preferably 70 to 200 nm.

The primary particles within the particles constituting the granules formed of the alumina composition may be a combination of two types of alumina particles having different average primary particle diameters. An example is a combination of NXA-100 and NXA-150, when NXA is employed, for example.

The particles constituting the granules formed of the alumina composition has a BET specific surface area of preferably 5 $m^2$/g or more, more preferably 7.5 $m^2$/g or more, even more preferably 8 $m^2$/g or more, as measured in compliance with JIS Z 8830:2013.

With a BET specific surface area of 5 $m^2$/g or more, it is easier to lower the sinterable temperature. This facilitates easier sintering, or makes it easier to inhibit the reduction in translucency due to the opacification occurring in the sintered body after sintering.

The BET specific surface area is preferably 25 $m^2$/g or less, more preferably 20 $m^2$/g or less, even more preferably 15 $m^2$/g or less.

With a BET specific surface area of 25 $m^2$/g or less, the average primary particle diameter is not excessively small, preventing the pre-sintered body from becoming overly hard. This facilitates a reduction in the amount of tool wear and/or chipping rate, or allows for a reduction of density coarseness by ensuring sufficient necking, making it easier to reduce the chipping rate.

An alumina composition of the present invention may employ a granular form in 50% or more, preferably 70% or more, more preferably 80% or more, even more preferably 90% or more of the alumina in the alumina composition.

When an alumina composition of the present invention does not employ a granular form, the alumina particles constituting the powder may have the average primary particle diameter and the BET specific surface area noted above.

The average particle diameter of granules in an alumina composition of the present invention (secondary particle diameter; hereinafter, also referred to as "average granule diameter") is preferably 10 μm or more, more preferably 12 μm or more, even more preferably 14 μm or more. When the average granule diameter is less than 10 μm, there is a risk of trapping air in the process of placing the granules in a die, leading to inadequate degassing during molding. This may result in the inability to fabricate a uniform and dense molded body. Additionally, there is a risk of granules being ejected through gaps during molding, potentially resulting in a molded body that does not meet the predetermined quantitative requirements. The average granule diameter is preferably 200 μm or less, more preferably 190 μm or less, even more preferably 180 μm or less, particularly preferably 150 μm or less, most preferably 100 μm or less. When the average granule diameter exceeds 200 μm, there is an increased likelihood of cavity formation within the granules. Additionally, voids are more likely to occur when placing the granules in a die. These phenomena pose a risk of inadequate degassing during molding, potentially resulting in the inability to fabricate a dense molded body. There is also a risk of increased shrinkage during molding, potentially leading to the inability to fabricate a molded body of the desired size.

It is preferable that 50% or more of the alumina in the alumina composition constitute granules. Preferably, the average granule diameter is measured using a method that does not disrupt the granules. The average granule diameter can be measured using a method, for example, such as dry sieving or wet sieving.

Measurement by dry sieving can be conducted following the test sieving described in JIS Z 8815:1994. Both manual sieving and mechanical sieving are applicable; however, mechanical sieving is preferred.

For sieving, the test sieve described in JIS Z 8801-1:2019 can be used.

Ro-Tap sieve shakers or sonic sieving analyzers may be used for sieving, for example. Examples of the Ro-Tap sieve shakers include RPS-105M manufactured by Seishin Enterprise Co., Ltd. Examples of the sonic sieving analyzers include Robot Sifter RPS-01 and Robot Sifter RPS-02 manufactured by Seishin Enterprise Co., Ltd.

It is preferable that granules in an alumina composition of the present invention have high sphericity. By increasing the sphericity of granules, it is possible to promote mixing at the interface between layers when stacking alumina powders of different compositions.

With increased sphericity, it is also possible to increase the packing density of when an alumina powder is filled into a mold to prepare a molded body, even when the average particle diameter is the same. The strength and translucency of the sintered body can increase by increasing the packing density, which is a density of a molded body formed into a specific shape under pressure after alumina granules are filled into a specific mold (such as a die).

It is also possible to more easily fill granules into angular portions when the mold have angular portions.

The sphericity of granules in an alumina composition of the present invention can be represented by parameters, for example, such as light bulk density, and heavy bulk density.

In view of increasing granule flow (ease of loading) to reduce coarseness in the density of the molded body obtained, an alumina composition of the present invention has a light bulk density of preferably 0.6 g/$cm^3$ or more, more preferably 0.7 g/$cm^3$ or more, even more preferably 0.8 g/$cm^3$ or more, particularly preferably 0.9 g/$cm^3$ or more.

The light bulk density can be measured in compliance with JIS R 9301-2-3:1999.

In view of increasing granule flow (ease of loading) to reduce coarseness in the density of the molded body obtained, an alumina composition of the present invention has a heavy bulk density of preferably 0.8 g/$cm^3$ or more, more preferably 0.9 g/$cm^3$ or more, even more preferably 1.0 g/$cm^3$ or more.

The heavy bulk density can be measured in compliance with JIS R 9301-2-3:1999.

An alumina composition of the present invention preferably comprises a binder.

The binder may be, for example, an organic binder.

Examples of the organic binder include common binders such as acrylic binders, acrylate binders, paraffinic binders, fatty acid binders, and polyvinyl alcohol binders.

Preferred among these organic binders is one having a carboxyl group in the molecular chain, or a derivative of carboxylic acids, more preferably an acrylic binder, even more preferably a polyacrylate having water solubility. The polyacrylate may be a product of copolymerization of acrylic acid or methacrylic acid with maleic acid, and may contain sulfonic acid. Examples of the cations of the salt include sodium and ammonium.

Depending on the content of the binder in an alumina composition of the present invention, it is possible to adjust the distance between primary particles in the alumina composition, the cumulative distribution of pores, and the relative density, making it easier to adjust the Vickers hardness or the strength of the pre-sintered body by increasing or decreasing these factors.

The binder content is preferably 1.2 to 2.8 mass %, more preferably 1.5 to 2.5 mass %, even more preferably 1.8 to 2.2 mass % in the whole alumina composition. When the binder content is 1.2 mass % or more in the whole alumina composition, the pre-sintered body does not become overly strong, eliminating the risk of hardening when removing the cut workpiece.

When the binder content is 2.8 mass % or less, the strength of the pre-sintered body does not overly decrease, reducing the possibility of the workpiece detaching during cutting, in addition to facilitating a reduction in chipping rate.

An alumina composition of the present invention may optionally comprise additives other than sintering aids (additives excluding $CeO_2$, $ZrO_2$, and $Y_2O_3$), such as colorants (including pigments, composite pigments, and fluorescent agents), titanium oxide ($TiO_2$), silica ($SiO_2$), dispersants, and antifoaming agents. These components may be used alone, or two or more thereof may be used as a mixture.

Examples of the pigments include oxides of at least one element selected from the group consisting of Ti, V, Cr, Mn, Fe, Co, Ni, Zn, Y, Zr, Sn, Sb, Bi, Ce, Sm, Eu, Gd, and Er.

Examples of the composite pigments include $(Zr,V)O_2$, $Fe(Fe,Cr)_2O_4$, $(Ni,Co,Fe)(Fe,Cr)_2O_4$—$ZrSiO_4$, and $(Co,Zn)Al_2O_4$.

Examples of the fluorescent agents include $Y_2SiO_5$:Ce, $Y_2SiO_5$:Tb, $(Y,Gd,Eu)BO_3$, $Y_2O_3$:Eu, YAG:Ce, $ZnGa_2O_4$:Zn, and $BaMgAl_{10}O_{17}$:Eu.

The additives may be added during mixing or pulverization, or may be added after pulverization.

A certain embodiment is, for example, an oxide ceramic pre-sintered body for dental use that, after being fired into a sintered body at 1,400° C. or less without hot isostatic pressing, shows a translucency (ΔL) of 9 or more as a sintered body of 1.2 mm thickness, and a total transmittance of 27% or more and a linear light transmittance of 0.5% or more as a sintered body of 1.0 mm thickness under a D65 illuminant. The translucency (ΔL), total transmittance, and linear light transmittance share the same measurement methods and preferred ranges as the translucency (ΔL), total transmittance, and linear light transmittance of the alumina sintered body described later.

Another certain embodiment is, for example, an oxide ceramic pre-sintered body for dental use that shows a number-based average crystal grain size of 0.3 to 8.0 μm after being fired into a sintered body at 1,400° C. or less without hot isostatic pressing.

The average crystal grain size shares the same measurement method and preferred ranges as the average crystal grain size of the alumina sintered body described later.

A certain embodiment is a method for producing an oxide ceramic pre-sintered body for dental use, comprising the steps of:

press molding an oxide ceramic composition under a surface pressure of 5 to 600 MPa; and firing the resultant molded body at 400 to 1,300° C. under atmospheric pressure, the oxide ceramic pre-sintered body for dental use comprising oxide ceramic particles with an average primary particle diameter of 50 to 300 nm, and having a D10 of 20 nm or more and a D90 of 90 nm or less in a cumulative distribution of pores.

Another certain preferred embodiment is, for example, a method for producing an oxide ceramic pre-sintered body for dental use in which the oxide ceramic particles comprise zirconia and/or alumina in the above method of producing an oxide ceramic pre-sintered body for dental use. Zirconia and alumina are as described for the pre-sintered body.

The following descriptions of an oxide ceramic pre-sintered body producing method of the present invention are given through the case of a method of producing an alumina pre-sintered body, taking aluminum oxide as an example of the oxide ceramic.

The method can be implemented in the same fashion as a method of producing a zirconia pre-sintered body when the oxide ceramic is zirconium oxide, except where specified otherwise.

An example of an alumina pre-sintered body producing method comprises the steps of:

producing an alumina composition comprising alumina particles and a sintering aid; and firing (pre-sintering) the alumina composition (for example, a molded body) to obtain an alumina pre-sintered body having an average primary particle diameter of 50 to 300 nm, and a D10 of 20 nm or more and a D90 of 90 nm or less in a cumulative distribution of pores within the pre-sintered body.

The content of the sintering aid is preferably 10 to 5,000 ppm.

The process of producing an alumina composition of the present invention is described first.

First, alumina and a sintering aid are mixed in predetermined proportions to prepare a mixture (mixing step). For example, when the sintering aid is magnesium chloride, alumina and magnesium chloride may be mixed at a mixing ratio that provides the foregoing contents. The mixing process may be dry mixing or wet mixing. In view of enabling the adjustment of the cumulative pore distribution and relative density, the alumina composition may be pulverized (preferably, crushed) until the foregoing average primary particle diameter is achieved (pulverization step).

The mixing and pulverization may be performed in a single step. Pulverization can be performed by using, for example, a ball mill or bead mill after dispersing the composition and binder in a solvent such as water or alcohol (dispersing step). In view of enabling the adjustment of the cumulative pore distribution and relative density, the composition of pulverized (preferably, crushed) to achieve an average primary particle diameter of, for example, 0.05 μm to 0.3 μm in the composition. For particle size adjustment, the composition may optionally be subjected to other processes (classification, elutriation).

The average primary particle diameter can be measured by laser diffraction/scattering particle size distribution analysis. For example, the average primary particle diameter can be measured by volume with ultrasonic waves being applied after a slurry diluted with water is subjected to 30 minutes of ultrasonication, using a laser diffraction/scattering particle size distribution analyzer (manufactured by Horiba Ltd. under the trade name Partica LA-950).

After the mixing and/or pulverization step, the mixture may be dried by spray drying with a spray dryer or the like to achieve the aforementioned granular form in the alumina composition (drying step).

In the pulverization step, the average primary particle diameter of the alumina composition is preferably less than 0.3 μm, more preferably 0.25 μm or less, even more preferably 0.2 μm or less, particularly preferably 0.15 μm or less. When the average primary particle diameter of the alumina composition is less than 0.15 μm, it is possible to enhance translucency in the sintered body after sintering while improving the machinability of the pre-sintered body.

Alumina and sintering aids may be separately prepared. For example, it is possible to independently provide separate preparation steps (for example, production steps) for alumina and sintering aids, instead of simultaneously precipitating alumina and sintering aids (in the same step). In this way, the aforementioned α-alumina can be obtained with high purity and a small primary particle diameter.

Generally, in the production of alumina compositions, sintering aids may be reacted with alumina through heat treatment, and the resulting product may be used for the pulverization and drying steps.

This enables the production of granules formed of the alumina composition, which serves as the raw material of alumina pre-sintered bodies.

The granule or powder can be formed into a molded body by applying an external force. The molding method is not limited to specific methods, and a suitable method may be appropriately selected according to intended use. For example, molding may be achieved by press molding, injection molding, stereolithography, slip casting, gel casting, filtration-casting, or casting. Molding may be performed in multiple stages.

For example, the alumina composition may be subjected to a CIP process after press molding, or press molding and CIP molding may be repeated.

Examples of the press molding method include a uniaxial pressing process (hereinafter, also referred to as "uniaxial pressing"), a biaxial pressing process, and a CIP (Cold Isostatic Pressing) process. These may be performed in combination, as needed.

A molded body of the present invention may have a disc shape, a cuboidal shape, or a shape of a dental product (for example, a crown shape).

A certain embodiment is, for example, a method for producing an oxide ceramic pre-sintered body for dental use in which the pressure molding is uniaxial pressing, and the uniaxial pressing involves a surface pressure of 5 to 600 MPa.

The molded body obtained through the pressure molding process may be, for example, a columnar molded body packed by uniaxially pressing the alumina granules filled into a die. The molded body can increase its density with higher surface pressure during press molding. Conversely, a hard alumina pre-sintered body results when the density of the molded body is excessively high. In view of enabling the adjustment of the cumulative pore distribution and relative density, the surface pressure in press molding is preferably 5 to 600 MPa, more preferably 10 to 400 MPa, even more preferably 15 to 200 MPa. When the surface pressure in the pressing process (for example, uniaxial pressing) is 5 MPa or more, the molded body exhibits superior shape retention. With a surface pressure of 600 MPa or less, it is possible to prevent excessive density increase in the molded body, making it easier to avoid hardening.

The preferred range of surface pressures in press molding may be 50 MPa or more, 80 MPa or more, 100 MPa or more, or 150 MPa or more, depending on factors such as the desired cumulative pore distribution and relative density.

A molded body of the present invention encompasses molded bodies compacted by a high-temperature pressing process such as a CIP (Cold Isostatic Pressing) process. In view of the above, the hydraulic pressure is preferably 50 to 1,000 MPa, more preferably 100 to 600 MPa, even more preferably 150 to 300 MPa.

The content of the alumina and sintering aids in an alumina pre-sintered body of the present invention is the same as that in the alumina composition to be fabricated into an alumina pre-sintered body. In view of the strength and translucency of sintered bodies fabricated from an alumina pre-sintered body of the present invention, preferred as sintering aids are magnesium compounds for their uniform dispersibility.

The following describes the step of firing (pre-sintering) the molded body under atmospheric pressure (pre-sintering step).

The firing temperature (hereinafter, also referred to as "pre-sintering temperature") in the pre-sintering step influences the Vickers hardness or the strength of the pre-sintered body.

The cumulative pore distribution and the hardness of the pre-sintered body undergo changes with the pre-sintering temperature combined with the alumina particles of a predetermined average primary particle diameter contained in the molded body, resulting in changes in the amount of tool wear and/or chipping rate.

In view of allowing particles to form necks while maintaining an appropriate distance, and achieving desired properties such as cumulative pore distribution and relative density, the pre-sintering temperature (highest pre-sintering temperature) in an alumina pre-sintered body producing method of the present invention is preferably 400 to 1,300° C., more preferably 500 to 1,200° C., even more preferably 600 to 1,100° C., particularly preferably 800 to 1,000° C.

Debinding of organic components can be achieved by processing at the highest pre-sintering temperature.

In certain embodiments, when the composition or molded body contains organic components, debinding of organic components may be achieved by conducting preliminary firing at a temperature lower than the highest pre-sintering temperature, before firing at the highest pre-sintering temperature.

The preliminary firing temperature is lower than the highest pre-sintering temperature, and is preferably 350° C. to 650° C., more preferably 400° C. to 600° C., even more preferably 450° C. to 550° C.

The preliminary firing temperature is held for a duration of preferably 15 minutes to 4 hours, more preferably 30 minutes to 3 hours, even more preferably 45 minutes to 2 hours.

When the pre-sintering temperature is 400° C. or more, the pillar (support or sprue) that connects a section of the pre-sintered body to the workpiece while it is being cut by machining the pre-sintered body can remain unbroken, preventing the workpiece from being detached during the cutting process. Additionally, the Vickers hardness can be adjusted within the desired range to reduce an increase in chipping rate.

When the pre-sintering temperature is 1,300° C. or less, there is no excessive neck formation, preventing the workpiece from becoming too hard. This facilitates a quicker separation of the workpiece from the frame securing the workpiece.

Additionally, an increase in chipping rate can be reduced as tool wear remains low, allowing for an easy separation of the workpiece from the pillar.

It is preferable to maintain the highest pre-sintering temperature for a certain time period because it confines the hardness of the pre-sintered body within the preferred range, and may lead to a reduction in chipping rate.

The pre-sintering conditions depend on the average primary particle diameter of the pre-sintered body, and the density of the pre-sintered body.

The holding time at the highest pre-sintering temperature may be 20 minutes to 8 hours. The preferred duration is 30 minutes to 6 hours.

Preferably, the rate of temperature increase to the highest pre-sintering temperature, and the rate of temperature decrease from the highest pre-sintering temperature are 300° C./min or less.

An alumina pre-sintered body of the present invention can be machined to fabricate a workpiece. The processing method is not limited to specific methods, and a suitable method may be appropriately selected according to intended use. For example, an alumina disc (pre-sintered body) can be milled or ground into a shape of a dental product (for example, a crown-shaped prosthesis) with a CAD/CAM system to fabricate a workpiece.

The surface smoothness of the workpiece can be improved using tools such as a PearlSurface© (manufactured by Kuraray Noritake Dental Inc.).

The processing machine used for machining a pre-sintered body of the present invention is not particularly limited. For example, milling machines such as desktop processing machines and large machining centers (general-purpose processing machine) may be used, depending on the workpiece to be cut. Examples of such milling machines include tabletop processing machines, for example, such as DWX-50, DWX-4, DWX-4W, DWX-52D, and DWX-52DCi (manufactured by Roland DG Corporation). Alternatively, a grinding process may be employed.

The tools employed in the processing machines for machining a pre-sintered body of the present invention are not particularly limited. Milling burs and grinding burs recommended by processing machine suppliers can be suitably used. A KATANA© drill represents an example of milling burs used for milling machines.

The lifetime of tools used in machining equipment is contingent on usage conditions. For example, when cutting the pre-sintered body, wearing of the drill blade (tool wear) may lead to problems such as the machined surface of the pre-sintered body fracturing into small pieces (chipping) or large pieces. This results in productivity-related issues such as a time-consuming rework of the machining process.

To assess tool life, torque on the machine side can be monitored, and a specific torque value may be established as the upper threshold limit, serving as an indicator to determine tool life (an indicator to decide when the tool should be replaced).

Alternatively, the machining time may serve as the upper threshold limit. Verification of tool life may involve, for example, measuring the wear width of the blade on the milling bur used in the milling machine. In the case of a KATANA© drill for example, the tool life (replacement time) can be identified when the wear width reaches 0.21 mm or more. The wear width of the blade is preferably within 0.2 mm, more preferably within 0.15 mm, even more preferably within 0.1 mm.

The following descriptions of an oxide ceramic sintered body producing method of the present invention are given through the case of a method of producing an alumina sintered body, taking aluminum oxide as an example of the oxide ceramic.

An alumina sintered body of the present invention can be fabricated by sintering an alumina pre-sintered body of the present invention, or a cut workpiece thereof, at a temperature that sinters the alumina particles (sintering step).

The sinterable temperature (for example, highest sintering temperature) is preferably higher than 1,300° C., and is variable according to the average primary particle diameter.

When the average primary particle diameter is approximately 100 nm, the sinterable temperature (for example, highest sintering temperature) is, for example, preferably higher than 1,300° C., more preferably 1,350° C. or more, even more preferably 1,375° C. or more.

The sinterable temperature is, for example, preferably 1,500° C. or less, more preferably 1,450° C. or less. The rate of temperature increase and the rate of temperature decrease are preferably 300° C./min or less.

In the sintering step, the holding time at the sinterable temperature (for example, highest sintering temperature) is preferably 120 minutes or less, more preferably 90 minutes or less, even more preferably 75 minutes or less, yet more preferably 60 minutes or less, particularly preferably 45 minutes or less, most preferably 30 minutes or less. The holding time is preferably 1 minute or more, more preferably 3 minutes or more, even more preferably 5 minutes or more.

An alumina composition and alumina pre-sintered body of the present invention enable a shorter sintering process to be employed for the fabrication of a sintered body, without causing a decrease in the translucency and strength of the alumina sintered body fabricated. Particularly, it is possible to shorten the holding time at the highest sintering temperature for the fabrication of a sintered body (short sintering). This enhances production efficiency, and when an alumina pre-sintered body of the present invention is applied to dental products, the patient can experience less time-related stress because it takes a shorter time before a treatment can be started with a dental product after its dimensions are determined and the product is milled for the treatment.

It is also possible to reduce the energy cost.

In the sintering step, the holding time at the sinterable temperature (for example, highest sintering temperature) may be, for example, 25 minutes or less, 20 minutes or less, or 15 minutes or less.

Preferably, the rate of temperature increase to the highest sintering temperature, and the rate of temperature decrease from the highest sintering temperature in the sintering process are set so as to reduce the time required for the sintering process. For example, the rate of temperature increase may be set so that the highest sintering temperature is reached in the shortest possible time, depending on the capabilities of the furnace. The rate of temperature increase to the highest sintering temperature may be, for example, 10° C./min or more, 50° C./min or more, 100° C./min or more, 120° C./min or more, 150° C./min or more, or 200° C./min or more. Preferably, the rate of temperature decrease is set to a rate that does not cause deformation due to shrinkage rate differences, or defects such as cracks, in the sintered body. For example, the sintered body may be allowed to cool at room temperature after the heating is finished.

A certain embodiment is, for example, a method for producing an oxide ceramic sintered body for dental use, comprising the step of sintering an oxide ceramic pre-sintered body under atmospheric pressure without a hot isostatic pressing process. In a method for producing an oxide ceramic sintered body for dental use according to the present invention, there is no need for a hot isostatic pressing (HIP) process. This eliminates the need for specialized equipment, allowing for easy production of an oxide ceramic sintered body for dental use.

The following descriptions of the oxide ceramic sintered body are given through the case of an alumina sintered body, taking aluminum oxide as an example of the oxide ceramic.

Here, “alumina sintered body” refers to, for example, a state where alumina particles (powder) have sintered.

The alumina sintered body has a relative density of preferably 99.5% or more.

The same applies to other oxide ceramic sintered bodies.

An alumina sintered body of the present invention encompasses not only sintered bodies of molded alumina particles sintered under ordinary pressure and no applied pressure, but also sintered bodies compacted by a high-temperature pressing process such as a HIP (Hot Isostatic Pressing) process.

A greater relative density in an alumina sintered body of the present invention leads to fewer internal voids and less scattering of light. Because this results in an alumina sintered body with increased translucency (ΔL), total transmittance, and linear light transmittance, and in view of improved aesthetics and strength, it is preferable for an alumina sintered body of the present invention to exhibit higher relative density.

An alumina sintered body of the present invention has a relative density of, for example, preferably higher than 95%, more preferably 98% or more, even more preferably 99.5% or more. Most preferably, an alumina sintered body of the present invention is essentially void free.

In view of superior translucency and strength, an alumina sintered body of the present invention has an average crystal grain size of preferably 0.3 to 8.0 μm, more preferably 0.4 to 6.0 μm, even more preferably 0.5 to 3.0 μm.

The method of measurement of average crystal grain size is as described in the EXAMPLES section below.

The content of alumina and sintering aids in an alumina sintered body of the present invention is the same as that in the composition and/or pre-sintered body to be fabricated into a sintered body.

An alumina sintered body of the present invention has a translucency (ΔL) of preferably 9 or more, more preferably 12 or more, even more preferably 15 or more, particularly preferably 20 or more.

Translucency (ΔL) takes a lightness value L* (color space) of L*a*b*color system (JIS Z 8781-4:2013), and it is a value after subtracting a second L* value from a first L* value, where the first L* value is an L* value measured for a 1.2 mm-thick sample (sintered body) against a white background, and the second L* value is an L* value measured for the same sample against a black background.

Samples for the measurement of translucency (ΔL) can be prepared as follows, for example. First, granules (composition) are press molded to provide a thickness of 1.2 mm for the sintered body to be produced, and subsequent CIP molding forms, for example, a disc-shaped molded body measuring 19 mm in diameter. The molded body can then be fired under predetermined firing conditions, and a sintered body, or a sample, having a thickness of 1.2 mm can be prepared by polishing the surface at #2000. For the measurement of L* values, a colorimeter (for example, CE100, analysis software Crystaleye manufactured by Olympus Corporation) can be used to measure L* values against black and white backgrounds after applying a contact liquid to a sample surface. The contact liquid may be, for example, one having a measured refractive index nD of 1.60 at 589 nm wavelength (sodium D-line).

In an alumina sintered body of the present invention, the total transmittance under a D65 illuminant is preferably 27% or more, more preferably 40% or more, even more preferably 55% or more, particularly preferably 60% or more for a sintered body of 1.0 mm thickness. The method of measurement of total transmittance is as described in the EXAMPLES section below.

In an alumina sintered body of the present invention, the linear light transmittance is preferably 0.5% or more, more preferably 0.7% or more, even more preferably 1.0% or more, particularly preferably 4.0% or more for a sintered body of 1.0 mm thickness.

The method of measurement of linear light transmittance is as described in the EXAMPLES section below.

An alumina sintered body of the present invention may be a molded body of a predetermined shape. For example, the sintered body may have a disc (discotic) shape, a cuboidal shape, or a shape of a dental product (for example, a crown shape).

The methods of production of the alumina compositions, granules, powders, molded bodies, pre-sintered bodies, cut workpieces, and sintered bodies described in the present specification are not limited those described above, and a variety of known methods are applicable, except where specified otherwise.

The present invention encompasses embodiments combining the foregoing features in various ways within the technical idea of the present invention, provided that the present invention can exhibit its effects.

In the present invention, the upper limits and lower limits of numeric ranges (for example, ranges of contents of components, ranges of various elements (such as the average primary particle diameter), and ranges of physical properties) can be appropriately combined.

EXAMPLES

The present invention is described below in greater detail. It should be noted, however, that the present invention is in no way limited by the following Examples, and various changes may be made by a person with ordinary skill in the art within the technical idea of the present invention.

[Measurement of Cumulative Distribution of Pores within Pre-Sintered Body]

The cumulative distribution of pores within pre-sintered bodies was measured at a pressure of 0.5 to 60,000 psia using an automatic mercury porosimeter (a pore distribution measurement device AutoPore© IV 9500 manufactured by Micromeritics, USA), in compliance with JIS R 1655:2003. The measurement was conducted after cutting pre-sintered bodies into 1.2 $cm^3$ samples (10.8 mm in diameter×13 mm in height).

[Measurement of Relative Density]

The methods described in the Examples and Comparative Examples below were used to acquire pre-sintered bodies measuring approximately 20 mm in length, 19 mm in width, and 17 mm in height, except for using a die of a different size for the pressing of granules.

For the measurement of the relative density of pre-sintered bodies, the pre-sintered bodies were cut into 1.2 $cm^3$ samples (10.8 mm in diameter×13 mm in height), and measured for porosity at a pressure of 0.5 to 60,000 psia using an automatic mercury porosimeter (a pore distribution measurement device AutoPore© IV 9500 manufactured by Micromeritics, USA), in compliance with JIS R 1655:2003. The relative density was calculated from the measured porosity, using the following formula.

$$(\text{Relative density})\,(\%) = \{1 - (\text{porosity})\} \times 100$$

[Measurement of Average Primary Particle Diameter of Pre-Sintered Body]

The pre-sintered bodies obtained in the Examples and Comparative Examples below were used to prepare surface images, using a scanning electron microscope (VE-9800 manufactured by Keyence under this trade name).

For the measurement of particle diameter, the SEM image with indicated primary particles was binarized with image analysis software (Image-Pro Plus manufactured by Hakuto Co., Ltd. under this trade name), and particles were recognized from the field (region) after indicating grain boundaries on individual crystal grains in the image.

In areas with unclear grain boundaries, a reduce filter was applied to the region until each region reduced to a single or multiple points, and Voronoi polygons were created by using these points as generators of Voronoi polygons. Lines were drawn that connect the midpoints between two adjacent generators, and these lines were superimposed on the original particle image to separate adjacent particles. For example, in the case where image processing produced a particle that looks like a gourd, the particle was separated into two by assuming that two adjoining circular particles are seen as a single particle.

In a processing file recognizing primary particle diameter, "Diameter" was selected from "Count/size dialog" to find the distribution (n=4). Specifically, a mean value of particle diameters (primary particle diameters) measured in each field with the image analysis software (Image-Pro Plus) was determined for four fields from one sample.

[Measurement of Amount of Tool Wear]

The methods described in the Examples and Comparative Examples below were used to acquire disc-shaped pre-sintered bodies measuring 14 mm in thickness and 98.5 mm in diameter, except for using a die of a different size for the pressing of granules.

Using three-dimensional NC data, the disc-shaped pre-sintered body was cut down to a 1 mm thick disc with an unused KATANA© drill (manufactured by Kuraray Noritake Dental Inc.; 2 mm in diameter, non-diamond coated), using a milling machine DWX-52DC manufactured by Kuraray Noritake Dental Inc. The drill was removed after milling and the amount of blade wear was measured at the drill tip using a light microscope.

Figure 2:
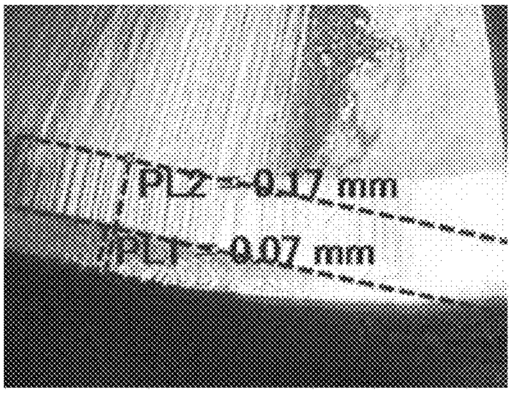
FIG. 2 A light micrograph of a KATANA© drill with 0.07 mm of tool wear according to Example 1.
Figure 3:
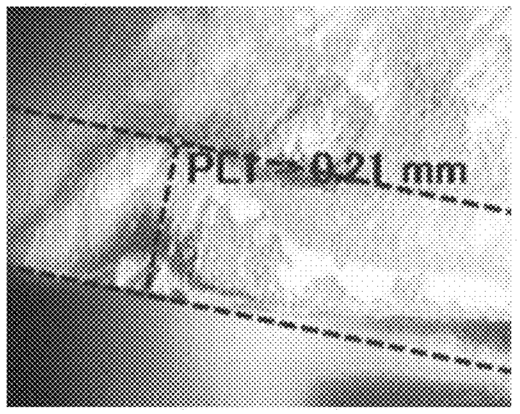
FIG. 3 A light micrograph of a KATANA© drill with 0.21 mm of tool wear according to Comparative Example 2.

FIG. 2 shows a light micrograph depicting the amount of tool wear in Example 1. FIG. 3 shows a light micrograph depicting the amount of tool wear in Comparative Example 2.

The machining was conducted in contour patterns with a spindle rotational speed of 30,000 rpm, a feed rate of 2,000 mm/min, a machining pitch of Z=0.5 mm, and XY=1 mm, outwardly from the center of the disc-shaped pre-sintered body.

[Measurement of Chipping Rate]

A light microscope was used to acquire a side-surface image of the 1 mm thick disc machined for the measurement of tool wear. The chipped region was rendered black, distinguishing it from the white area outside the black area (binarized).

The chipping rate was determined as a percentage of the black area relative to the combined black and white areas.

Image analysis software (manufactured by Hakuto Co., Ltd. under the trade name Image-Pro Plus) was used for the area measurement.

The assessment criteria are as follows (n=4). Mean values were calculated for n=4, and the results marked as "Excellent", "Good", and "Moderate" were deemed acceptable.

<Assessment Criteria>

Excellent: 3% or less

Good: Greater than 3% and 7% or less

Moderate: Greater than 7% and 10% or less

Poor: Greater than 10%

Figure 4:
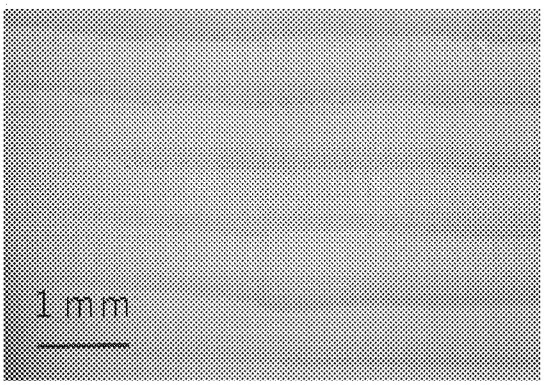
FIG. 4 A light micrograph showing a surface of a cut workpiece with a chipping rate of 3% or less according to Example 1.
Figure 5:
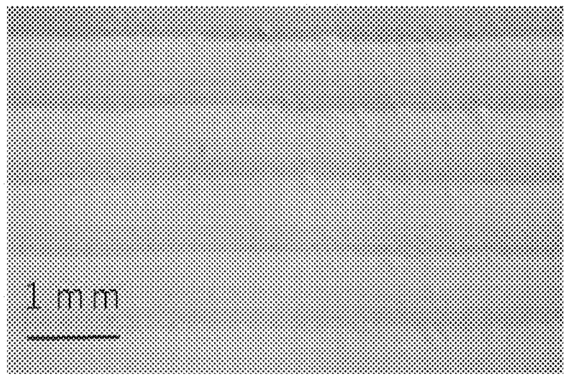
FIG. 5 A light micrograph showing a surface of a cut workpiece with a chipping rate of 10% or more according to Comparative Example 1

FIG. 4 shows a light micrograph depicting a captured surface of a cut workpiece with a chipping rate of 3% according to Example 1. FIG. 5 shows a light micrograph depicting a captured surface of a cut workpiece with a chipping rate of 10% according to Comparative Example 1.

[Measurement of Vickers Hardness of Pre-Sintered Body]

The pre-sintered bodies obtained in the Examples and Comparative Examples below underwent measurement in compliance with JIS Z 2244:2020. The measurement was conducted by applying and maintaining a load of 5 kgf for a duration of 30 seconds using a FALCON 500 manufactured by Innovatest, and the HV value was calculated (a mean value for n=10).

[Measurement of Sintering Aid Content]

The measurement was conducted using samples from the compositions, pre-sintered bodies, or sintered bodies obtained in the Examples and Comparative Examples below.

For the measurement, a field-emission scanning electron microscope (FE-SEM Reglus 8220, manufactured by Hitachi High-Tech Corporation) and an energy dispersive X-ray analyzer (Aztec Energy X-Max 50, manufactured by Oxford Instruments) were used under the following conditions (a mean value for n=3).

Measurement magnification: 5,000×

Analysis mode: surface analysis

Acceleration voltage: 5 kV

Working distance: 15 mm±1 mm

X-ray extraction angle: 30 degrees

Dead time: 7%

Measurement time: 100 seconds

[Strength Measurement of Pre-Sintered Body]

Disc-shaped pre-sintered bodies measuring 14 mm in thickness and 98.5 mm in diameter were cut into samples (5 mm×10 mm×50 mm) similar to those used for the measurement of tool wear, in compliance with ISO 6872:2015. For surface finishing, the sample surfaces, including chamfered surfaces (45° chamfers at the corners of sample; see ISO 6872:2015, Section 7.3.1.2.1), were finished longitudinally with #600 sandpaper.

The sample was disposed in such an orientation that its widest face was perpendicular to the vertical direction (loading direction), and was measured for three-point flexural strength at a span (the distance between supports) of 30 mm and a crosshead speed of 0.5 mm/min, using a universal testing machine (AG-I 100 kN manufactured by Shimadzu Corporation) (a mean value for n=3).

[Measurement of Specific Surface Area of Pre-Sintered Body]

For the measurement of BET specific surface area, the specific surface area of pre-sintered bodies was measured in compliance with JIS Z 8830:2013 under the following conditions, using a full automatic specific surface area analyzer (Macsorb© HM model-1201 manufactured by Mountech Co., Ltd. under this trade name; BET flow method (single-point method)) (a mean value for n=3).

Carrier gas: helium (He)

Coolant: liquid nitrogen (N2)

Adsorbate gas: Nitrogen (N2)

Nitrogen concentration in helium-nitrogen mixture gas: 30.39%

Gas flow rate: 25 ml/m

Concurrent relative pressure P/PO=0.2948

[Measurement Method of Average Crystal Grain Size of Alumina Sintered Body]

The alumina sintered bodies obtained in the Examples and Comparative Examples were photographed to capture surface images, using a scanning electron microscope (VE-9800 manufactured by Keyence under this trade name). The crystal grain size of crystal grains was measured by image analysis after indicating grain boundaries on individual crystal grains in the image.

For the measurement of crystal grain size, the captured SEM image was binarized with image analysis software (Image-Pro Plus manufactured by Hakuto Co., Ltd. under this trade name), and particles were recognized from the field (region) by adjusting the brightness range to provide clear grain boundaries.

The crystal grain size from Image-Pro Plus is the average of the measurements of the length of a line segment connecting the contour line and passing through the center of gravity determined from the contour line of the crystal grain, conducted at 2-degree intervals with the center of gravity as the central point.

The measurement of crystal grain size was conducted for all particles not extending beyond the edges of the SEM photographic image (3 fields) in each Example and Comparative Example.

The average crystal grain diameter was calculated from the crystal grain size of each particle and the number of crystal grains. The resulting arithmetic average diameter was then determined as the average crystal grain size of the sintered body.

Note that particles not extending beyond the edges of the image are particles excluding those with contour lines extending beyond the screen of the SEM photographic image (particles with their contour lines interrupted by the boundary lines at the top, bottom, left, and right). To select the crystal grain size of all particles not extending beyond the edges of the image, the option in Image-Pro Plus was used that excludes particles lying on the boundary lines.

[Evaluation Method of Shrinkage Uniformity]

The methods described in the Examples and Comparative Examples below were used to acquire disc-shaped pre-sintered bodies measuring 14 mm in thickness and 98.5 mm in diameter, except for using a die of a different size for the pressing of granules.

By taking the thickness direction of the disc-shaped pre-sintered body as the Z axis, the X axis and Y axis were arbitrarily designated on the plane perpendicular to the Z axis.

This was followed by CAD/CAM processing of the disc-shaped pre-sintered body, cutting out fifteen cubes measuring 5 mm on each side, parallel to the X, Y, and Z axes. These cubes were identified as n=1, 2, 3, . . . , 15.

Before sintering, the dimensions of each cube, representing a workpiece, were measured, and denoted as X1, X2, . . . , X15, Y1, Y2, . . . , Y15, and Z1, Z2, . . . , Z15. Subsequently, all fifteen pieces were subjected to sintering under uniform conditions at the highest sintering temperatures presented in Table 3, resulting in the formation of sintered bodies.

In each Example and Comparative Example, the dimensions were also measured for all fifteen workpieces after sintering, and denoted as X'1, X'2, . . . , X'15, Y'1, Y'2, . . . , Y'15, and Z'1, Z'2, . . . , Z'15.

The shrinkage rate (S) of each workpiece can be determined for each of the X, Y, and Z axes as S=(dimensions after sintering)/(dimensions before sintering). For example, SX1=X'1/X1.

In this specification, "shrinkage rate (S)" refers to the ratio of the size of the workpiece after sintering and shrinkage to the size of the workpiece before sintering.

The average shrinkage rate can be determined by averaging the shrinkage rates for each of the X, Y, and Z axes. For example, it is the average of SX1 to SX15.

The uniformity of shrinkage can be determined by subtracting the average of all fifteen shrinkage rates from the shrinkage rate of each cube at the same position on the identical side.

For example, (shrinkage uniformity on X axis)=SXn−(average of SX1 to 15) (n=1 to 15).

As an indicator of shrinkage uniformity, values obtained from the formula for "shrinkage uniformity on X axis" (deviation of shrinkage rates) were evaluated individually (n=1 to 15). When all fifteen values fell within ±0.4%, it was considered as having high shrinkage uniformity (marked as "Good"). When any of these values exceeded+0.4%, it was considered as having low shrinkage uniformity (marked as Poor").

[Measurement Method of Translucency of Alumina Sintered Body]

The alumina sintered bodies obtained were ground into plate samples with a thickness of 1.2 mm. The samples were then measured for first lightness (Lw*) and second lightness (LB*) by using a spectrophotometer (manufactured by Olympus Corporation under the trade name Crystaleye) in 7-band measurement mode with an LED light source. The first lightness (Lw*) is the lightness resulting from the measurement of chromaticity against a white background, and the second lightness (LB*) is the lightness resulting the chromaticity measurement of the same sample conducted against a black background using the same measurement device in the same measurement mode with the same light source. The difference between these values (ΔL=(Lw*)−(LB*)) was determined as the translucency (ΔL) (a mean value for n=3).

The white background means the white part of the hiding-power test paper described in JIS K 5600-4-1:1999, Part 4, Section 1, and the black background means the black part of the hiding-power test paper.

[Measurement Method of Total Transmittance and Linear Light Transmittance of Alumina Sintered Body]

The alumina sintered bodies of Examples and Comparative Examples were measured for total transmittance and linear light transmittance in each layer. The alumina sintered bodies used for the measurement were prepared as follows.

First, molded bodies were fabricated from the raw material powder of each Example and Comparative Example by pressing the powder in a die having a diameter of 30 mm. Here, the raw material powder was introduced into the die in adjusted amounts to ensure the production of alumina sintered bodies with a thickness of 1.0 mm.

The molded bodies were fabricated following the methods described in Examples and Comparative Examples, except for replacing the die.

Alumina pre-sintered bodies were also fabricated following the methods described in Examples and Comparative Examples, except for using these molded bodies.

Subsequently, the alumina pre-sintered bodies were sintered into alumina sintered bodies by being held for 2 hours at the highest sintering temperatures presented in Table 3.

The alumina sintered bodies were polished to a mirror finish on both sides to prepare alumina sintered bodies with a thickness of 1.0 mm. These alumina sintered bodies were then measured for total transmittance and linear light transmittance with a turbidimeter (Haze Meter NDH 4000 manufactured by Nippon Denshoku Industries Co., Ltd.).

The measurement was conducted according to ISO 13468-1 and JIS K 7361-1:1997, and measured values were averaged for n=3. The results are presented in Table 3.

Example 1

After weighing 100 g of α-alumina raw material NXA-100 (manufactured by Sumitomo Chemical Co., Ltd.) and an equivalent to 0.1 g of magnesium chloride, these were introduced into 1 L of ethanol and ultrasonically dispersed.

These were introduced into a rotary container along with alumina beads, and the alumina raw material, including aggregated particles, was pulverized with a ball mill until the desired average primary particle diameter was achieved through mixing and crushing. The average primary particle diameter was measured by volume with ultrasonic waves being applied after a slurry diluted with ethanol was subjected to 30 minutes of ultrasonication, using a laser diffraction/scattering particle size distribution analyzer (manufactured by Horiba Ltd. under the trade name Partica LA-950). The desired slurry with hardly any secondary aggregation was obtained after about 1 hour of ball milling.

Subsequently, an organic binder was added to the slurry.

An aqueous acrylic binder, serving as the organic binder, was added in an amount of 2.5 mass % with respect to the α-alumina raw material (the organic binder content relative to the entire slurry). The mixture underwent stirring with rotary vanes for 24 hours.

After stirring, the slurry underwent drying and granulation with a spray dryer to yield alumina granules. The granules had an average particle diameter of 40 μm. The powder formed by these granules was introduced into a die of a predetermined size, and uniaxially pressed at 150 MPa under atmospheric pressure to yield a molded body.

The molded body was placed in an electric furnace, and heated from room temperature at 10° C./min. Following a 2-hour retention at 500° C. for the purpose of debinding organic components, the molded body underwent a temperature increase at 10° C./min to the pre-sintering temperature presented in Table 2. It was maintained at the pre-sintering temperature for 6 hours, and gradually cooled at −0.4° C./min to yield a pre-sintered body.

Subsequently, the pre-sintered body underwent sintering in an atmospheric environment by being retained for 2 hours at the highest sintering temperature presented in Table 2, yielding a sintered body.

Examples 2 to 4

The same procedure employed in Example 1 was used to obtain pre-sintered bodies, with the exception that NXA-100 or 150 (manufactured by Sumitomo Chemical Co., Ltd.) was used as the α-alumina raw material, and that pre-sintering was carried out at the highest pre-sintering temperatures presented in Table 2.

Similarly, sintered bodies were obtained following the procedure of Example 1, except for varying the highest sintering temperature as shown in Table 3.

Comparative Example 1

The same procedure employed in Example 2 was used to obtain a pre-sintered body and sintered body, with the exception that AA-03 (manufactured by Sumitomo Chemical Co., Ltd.) was used as the α-alumina raw material, instead of NXA-100.

Example 8, Comparative Example 2

After weighing 100 g of α-alumina raw material NXA-100 (manufactured by Sumitomo Chemical Co., Ltd.) and an equivalent to 0.1 g of magnesium chloride, these were introduced into 1 L of ethanol and ultrasonically dispersed.

These were introduced into a rotary container along with alumina beads, and the raw material was pulverized with a ball mill until the desired primary particle diameter was achieved through mixing and crushing. The average primary particle diameter was measured by volume with ultrasonic waves being applied after a slurry diluted with ethanol was subjected to 30 minutes of ultrasonication, using a laser diffraction/scattering particle size distribution analyzer (manufactured by Horiba Ltd. under the trade name Partica LA-950). The desired slurry with hardly any secondary aggregation was obtained after about 1 hour of ball milling.

The slurry underwent stirring in a 2 L beaker using rotary vanes at 200 rpm for 1 hour. Following an abrupt cessation of rotary vanes movement, the slurry was left to stand for 15 minutes. Settling of white particles was visible at the bottom of the beaker, and the supernatant appeared cloudy. The upper third of the slurry within the beaker was extracted as the slurry for Comparative Example 2, while the lower third of the slurry within the beaker was used as the slurry for Example 8. In Table 1, the distinction between slurries is based on elutriation, with Comparative Example 2 labeled as "Above NXA-100 elutriation", and Example 8 designated as "Below NXA-100 elutriation".

Subsequently, an organic binder was added to each slurry.

An aqueous acrylic binder, serving as the organic binder, was added in an amount of 2.5 mass % with respect to the α-alumina raw material (the organic binder content relative to the entire slurry). The mixture underwent stirring with rotary vanes for 24 hours. After stirring, the slurries underwent drying and granulation with a spray dryer, yielding two types of granules.

The two types of granules, representing "above NXA-100 elutriation" and "below NXA-100 elutriation", both had an average particle diameter of approximately 40 μm. The powder formed by each granule was introduced into a die of a predetermined size, and uniaxially pressed at 150 MPa to yield a molded body. The molded body was placed in an electric furnace, and heated from room temperature at 10° C./min. Following a 2-hour retention at 500° C. for the purpose of debinding organic components, the molded body underwent a temperature increase at 10° C./min to the pre-sintering temperature presented in Table 2. It was maintained at the pre-sintering temperature for 6 hours, and gradually cooled at −0.4° C./min from the highest pre-sintering temperature to yield pre-sintered bodies for Example 8 and Comparative Example 2.

Similarly, sintered bodies were obtained following the procedure of Example 1, except for varying the highest sintering temperature as shown in Table 3.

Examples 5 to 7

In Example 5, the pre-sintered body was obtained following the same procedure employed in Example 1.

In Examples 6 and 7, the pre-sintered bodies were obtained following the procedure of Example 1, with the exception that the sintering aid was used in the amounts presented in Table 1.

Subsequently, sintered bodies were obtained in an atmospheric environment following the same procedure employed in Example 1 using the NORITAKE KATANA System KATANA© F-1 N (manufactured by Kuraray Noritake Dental Inc.), except that the highest sintering temperature was varied as shown in Table 3.

Example 9

The pre-sintered body was obtained following the procedure of Example 1, with the exception that pre-sintering was carried out at the pre-sintering temperature presented in Table 2.

Similarly, the sintered body was obtained in the same manner as in Example 1, except that the highest sintering temperature was varied as shown in Table 3.

Examples 10 to 12

The pre-sintered bodies were obtained following the procedure of Example 1, except that the raw materials presented in Table 1 were used as α-alumina raw materials, instead of NXA-100, and that the pre-sintered bodies were produced under the conditions presented in Table 2.

In Example 10, the molded body after pressing was placed in an electric furnace, and heated from room temperature at 10° C./min to the pre-sintering temperature shown in Table 2. Following a 6-hour retention at the pre-sintering temperature, the molded body was gradually cooled at −0.4° C./min to yield a pre-sintered body.

The sintered body was obtained following the procedure of Example 1, except for varying the highest sintering temperature as shown in Table 3.

Comparative Example 3

The pre-sintered body was obtained following the procedure of Example 8, except that the pre-sintered body was produced under the conditions presented in Table 2.

The sintered body was obtained using the same method employed in Example 8.

Example 13

The pre-sintered body and sintered body were obtained in the same manner as in Example 1, with the exception that the molded body was obtained by uniaxial pressing under a reduced pressure of 80 kN, using a vacuum press molding machine (manufactured by IWAKI INDUSTRY Co., Ltd. under the trade name 250-Ton Vacuum Press Molding Machine).

Examples 14 to 18

The pre-sintered bodies were obtained in the same manner as in Example 1, except that different sintering aids were used in different amounts as shown in Table 1.

Subsequently, sintered bodies were obtained in an atmospheric environment following the same procedure employed in Example 1 using the NORITAKE KATANA System KATANA© F-1 N (manufactured by Kuraray Noritake Dental Inc.), except that the highest sintering temperature was varied as shown in Table 3.

The results for Examples and Comparative Examples are presented in Tables 2 and 3.

TABLE 1

| | Composition | | | | | | |
|---|---|---|---|---|---|---|---|
| | | Sintering aid[1)] | | | | | |
| | | Sintering aid 1 | | Sintering aid 2 | | Sintering aid 3 | |
| | Main ingredient | Type | Amount [ppm] | Type | Amount [ppm] | Type | Amount [ppm] |
| Ex. 1 | NXA-100 | $MgCl_2$ | 1000 | — | — | — | — |
| Ex. 2 | NXA-100 | $MgCl_2$ | 1000 | — | — | — | — |
| Ex. 3 | NXA-150 | $MgCl_2$ | 1000 | — | — | — | — |
| Ex. 4 | NXA-150 | $MgCl_2$ | 1000 | — | — | — | — |
| Ex. 5 | NXA-100 | $MgCl_2$ | 1000 | — | — | — | — |
| Ex. 6 | NXA-100 | $MgCl_2$ | 150 | — | — | — | — |
| Ex. 7 | NXA-100 | $MgCl_2$ | 50 | — | — | — | — |
| Ex. 8 | Below NXA-100 elutriation | $MgCl_2$ | 1000 | — | — | — | — |
| Ex. 9 | NXA-100 | $MgCl_2$ | 1000 | — | — | — | — |
| Ex. 10 | AKP-53 | $MgCl_2$ | 1000 | — | — | — | — |
| Ex. 11 | AA-04 | $MgCl_2$ | 1000 | — | — | — | — |
| Ex. 12 | NXA-150 | $MgCl_2$ | 1000 | — | — | — | — |
| Ex. 13 | NXA-100 | $MgCl_2$ | 1000 | — | — | — | — |
| Ex. 14 | NXA-100 | $Mg(OH)_2$ | 100 | — | — | — | — |
| Ex. 15 | NXA-100 | $ZrO_2$ | 100 | — | — | — | — |
| Ex. 16 | NXA-100 | $ZrO_2$ | 500 | $Y_2O_3$ | 57 | — | — |
| Ex. 17 | NXA-100 | $MgCl_2$ | 200 | $ZrO_2$ | 500 | $Y_2O_3$ | 57 |
| Ex. 18 | NXA-100 | $MgCl_2$ | 1000 | $ZrO_2$ | 1000 | $Y_2O_3$ | 113 |
| Com. Ex. 1 | AA-03 | $MgCl_2$ | 1000 | — | — | — | — |
| Com. Ex. 2 | Above NXA-100 elutriation | $MgCl_2$ | 1000 | — | — | — | — |
| Com. Ex. 3 | Below NXA-100 elutriation | $MgCl_2$ | 1000 | — | — | — | — |

[1)]The amount of sintering aid represents a value in terms of an element (for example, Mg equivalent when the sintering aid is $MgCl_2$.)

TABLE 2

| | Pre-sintered body | | | | | | | | | | | | |
|---|---|---|---|---|---|---|---|---|---|---|---|---|---|
| | Production conditions | | | | | | | | | | | | |
| | Pressing environment | Applied pressure [MPa] | Pre-sintering temperature1) [° C.] | Average primary particle diameter [nm] | Relative density [%] | Cumulative distribution of pores D10 [nm] | D90 [nm] | D10/D90 | BET specific surface area [m²/g] | Strength [MPa] | Vickers hardness [HV] | Amount of tool wear [mm] | Chipping rate [%] |
| Ex. 1 | Atm | 150 | 800 | 100 | 51 | 36 | 64 | 0.56 | 15 | 25 | 62 | 0.07 | Excellent |
| Ex. 2 | Atm | 150 | 1000 | 110 | 51 | 39 | 66 | 0.59 | 14 | 45 | 321 | 0.14 | Good |
| Ex. 3 | Atm | 150 | 800 | 150 | 52 | 39 | 79 | 0.49 | 12 | 13 | 47 | 0.02 | Good |
| Ex. 4 | Atm | 150 | 1000 | 150 | 52 | 40 | 79 | 0.51 | 11 | 38 | 287 | 0.12 | Good |
| Ex. 5 | Atm | 150 | 800 | 100 | 51 | 36 | 64 | 0.56 | 15 | 25 | 62 | 0.07 | Excellent |
| Ex. 6 | Atm | 150 | 800 | 100 | 51 | 35 | 63 | 0.56 | 15 | 26 | 64 | 0.07 | Good |
| Ex. 7 | Atm | 150 | 800 | 100 | 51 | 35 | 63 | 0.56 | 15 | 27 | 66 | 0.07 | Good |
| Ex. 8 | Atm | 150 | 1000 | 200 | 53 | 39 | 88 | 0.44 | 8 | 45 | 331 | 0.14 | Moderate |
| Ex. 9 | Atm | 150 | 600 | 100 | 50 | 35 | 62 | 0.56 | 16 | 10 | 24 | 0.01 | Moderate |
| Ex. 10 | Atm | 100 | 400 | 170 | 45 | 24 | 76 | 0.32 | 28 | 16 | 49 | 0.02 | Moderate |
| Ex. 11 | Atm | 50 | 1300 | 290 | 55 | 29 | 86 | 0.34 | 4.5 | 41 | 243 | 0.19 | Moderate |
| Ex. 12 | Atm | 15 | 1200 | 150 | 52 | 41 | 82 | 0.50 | 12 | 53 | 370 | 0.16 | Moderate |
| Ex. 13 | Reduced pressure | 150 | 800 | 100 | 53 | 40 | 81 | 0.49 | 15 | 27 | 64 | 0.09 | Excellent |
| Ex. 14 | Atm | 150 | 800 | 100 | 51 | 38 | 67 | 0.57 | 15 | 25 | 60 | 0.07 | Good |
| Ex. 15 | Atm | 150 | 800 | 100 | 52 | 41 | 82 | 0.50 | 15 | 28 | 69 | 0.12 | Good |
| Ex. 16 | Atm | 150 | 800 | 100 | 51 | 41 | 83 | 0.49 | 15 | 29 | 71 | 0.14 | Good |
| Ex. 17 | Atm | 150 | 800 | 100 | 52 | 39 | 80 | 0.49 | 15 | 28 | 70 | 0.14 | Good |
| Ex. 18 | Atm | 150 | 800 | 100 | 51 | 38 | 78 | 0.49 | 15 | 32 | 75 | 0.16 | Good |
| Com. Ex. 1 | Atm | 150 | 1000 | 400 | 55 | 19 | 79 | 0.24 | 5.5 | 9 | 29 | 0.02 | Poor |
| Com. Ex. 2 | Atm | 150 | 800 | 40 | 50 | 18 | 55 | 0.33 | 22 | 56 | 510 | 0.21 | Good |
| Com. Ex. 3 | Atm | 10 | 1000 | 200 | 41 | 36 | 92 | 0.39 | 10 | 9 | 331 | 0.02 | Moderate |

1)Highest pre-sintering temperature

TABLE 3

| | Sintered body | | | | | |
|---|---|---|---|---|---|---|
| | Highest sintering temperature [° C.] | Average crystal grain size [nm] | Shrinkage uniformity [—] | Translucency (ΔL) | Total transmittance [%] | Linear light transmittance [%] |
| Ex. 1 | 1375 | 0.8 | Good | 30.3 | 73.0 | 11.2 |
| Ex. 2 | 1400 | 0.8 | Good | 28.2 | 71.3 | 10.5 |
| Ex. 3 | 1400 | 0.9 | Good | 25.4 | 66.9 | 8.2 |
| Ex. 4 | 1400 | 0.9 | Good | 23.1 | 64.2 | 7.8 |
| Ex. 5 | 1450 | 0.9 | Good | 26.8 | 70.1 | 9.8 |
| Ex. 6 | 1450 | 1.9 | Good | 19.4 | 51.2 | 1.2 |
| Ex. 7 | 1450 | 2.5 | Good | 15.5 | 30.5 | 0.8 |
| Ex. 8 | 1400 | 1.0 | Good | 21.8 | 55.7 | 1.6 |
| Ex. 9 | 1400 | 0.8 | Good | 27.8 | 70.5 | 10.1 |
| Ex. 10 | 1325 | 0.8 | Good | 14.8 | 32.6 | 0.5 |
| Ex. 11 | 1400 | 0.7 | Good | 12.6 | 30.1 | 0.5 |
| Ex. 12 | 1400 | 1.3 | Good | 20.1 | 52.9 | 0.7 |
| Ex. 13 | 1375 | 0.8 | Good | 31.3 | 74.2 | 11.4 |
| Ex. 14 | 1450 | 2.2 | Good | 18.4 | 45.6 | 0.9 |
| Ex. 15 | 1450 | 2.4 | Good | 15.9 | 40.4 | 0.8 |
| Ex. 16 | 1450 | 2.3 | Good | 16.6 | 43.2 | 0.8 |
| Ex. 17 | 1450 | 1.9 | Good | 19.7 | 48.4 | 0.9 |
| Ex. 18 | 1450 | 1.8 | Good | 20.6 | 50.3 | 0.9 |
| Com. Ex. 1 | 1400 | 2.9 | Good | 3.5 | 20.2 | 0.0 |
| Com. Ex. 2 | 1400 | 0.8 | Good | 28.2 | 68.3 | 9.1 |
| Com. Ex. 3 | 1400 | 0.8 | Poor | 8.9 | 23.5 | 0.3 |

INDUSTRIAL APPLICABILITY

An oxide ceramic pre-sintered body for dental use of the present invention can be suitably used for machining such as CAD/CAM.

The invention claimed is:

1. An alumina pre-sintered body for dental use comprising alumina particles with an average primary particle diameter of 50 to 300 nm, and pores, and having a D10 of 20 nm or more and a D90 of 90 nm or less in a cumulative distribution of pores.

2. The alumina pre-sintered body for dental use according to claim 1, which has a relative density of 43 to 63%.

3. The alumina pre-sintered body for dental use according to claim 1, which has a BET specific surface area of 5 to 25 $m^2/g$ as measured in compliance with JIS Z 8830:2013.

4. The alumina pre-sintered body for dental use according to claim 1, which has a three-point flexural strength of 10 to 50 MPa as measured in compliance with JIS R 1601:2008.

5. The alumina pre-sintered body for dental use according to claim 1, which has a Vickers hardness of 350 HV 5/30 or less as measured in compliance with JIS Z 2244:2020.

6. The alumina pre-sintered body for dental use according to claim 1, wherein the alumina particles comprise α-alumina with a purity of 99.5% or more.

7. The alumina pre-sintered body for dental use according to claim 1, further comprising a sintering aid, wherein the sintering aid comprises at least one element selected from the group consisting of a Group 2 element, Ce, Zr, and Y.

8. The alumina pre-sintered body for dental use according to claim 1, which, after being fired into a sintered body at 1,400° C. or less without hot isostatic pressing, shows a translucency (ΔL) of 9 or more as a sintered body of 1.2 mm thickness, and a total transmittance of 27% or more and a linear light transmittance of 0.5% or more as a sintered body of 1.0 mm thickness under a D65 illuminant.

9. The alumina pre-sintered body for dental use according to claim 1, which shows a number-based average crystal grain size of 0.3 to 8.0 μm after being fired into a sintered body at 1,400° C. or less without hot isostatic pressing.

10. The alumina pre-sintered body for dental use according to claim 1, wherein the pre-sintered body does not comprise zirconia.

11. A method for producing an alumina sintered body for dental use, comprising sintering the alumina pre-sintered body of claim 1 under atmospheric pressure without hot isostatic pressing.

12. A method for producing the alumina pre-sintered body according to claim 1, comprising:

press molding a composition comprising alumina particles under a surface pressure of 5 to 600 MPa; and firing the resultant molded body at 400 to 1,300° C. under atmospheric pressure, wherein the alumina particles have an average primary particle diameter of 50 to 300 nm, and have a D10 of 20 nm or more and a D90 of 90 nm or less in a cumulative distribution of pores.

13. The method for producing an alumina pre-sintered body for dental use according to claim 11, wherein the alumina particles comprise α-alumina with a purity of 99.5% or more.

14. A method for producing an alumina sintered body for dental use, comprising sintering the alumina pre-sintered body produced by the method of claim 12 under atmospheric pressure without hot isostatic pressing.

15. The method for producing an alumina pre-sintered body for dental use according to claim 12, wherein the pre-sintered body does not comprise zirconia.

* * * * *